US012139751B2

(12) United States Patent
Hernández Neuta et al.

(10) Patent No.: US 12,139,751 B2
(45) Date of Patent: Nov. 12, 2024

(54) CIRCULARIZABLE PROBES FOR IN SITU ANALYSIS

(71) Applicant: 10x Genomics, Inc., Pleasanton, CA (US)

(72) Inventors: Jorge Iván Hernández Neuta, Stockholm (SE); Malte Kühnemund, Stockholm (SE); Jessica Östlin, Stocksund (SE); Xiaoyan Qian, Stockholm (SE); Toon Verheyen, Solna (SE)

(73) Assignee: 10X GENOMICS, INC., Pleasanton, CA (US)

(*) Notice: Subject to any disclaimer, the term of this patent is extended or adjusted under 35 U.S.C. 154(b) by 0 days.

(21) Appl. No.: 17/877,695

(22) Filed: Jul. 29, 2022

(65) Prior Publication Data

US 2023/0031996 A1 Feb. 2, 2023

Related U.S. Application Data

(60) Provisional application No. 63/277,106, filed on Nov. 8, 2021, provisional application No. 63/227,829, filed on Jul. 30, 2021.

(51) Int. Cl.
*C12Q 1/6841* (2018.01)
*C12Q 1/6855* (2018.01)

(52) U.S. Cl.
CPC ......... *C12Q 1/6841* (2013.01); *C12Q 1/6855* (2013.01); *C12Q 2600/16* (2013.01)

(58) Field of Classification Search
CPC ............... C12Q 1/6841; C12Q 1/6855; C12Q 2600/16; C12Q 1/682
See application file for complete search history.

(56) References Cited

U.S. PATENT DOCUMENTS

| | | |
|---|---|---|
| 4,318,846 A | 3/1982 | Khanna et al. |
| 4,683,195 A | 7/1987 | Mullis et al. |
| 4,683,202 A | 7/1987 | Mullis |
| 4,757,141 A | 7/1988 | Fung et al. |
| 4,800,159 A | 1/1989 | Mullis et al. |
| 4,849,336 A | 7/1989 | Miyoshi et al. |
| 4,965,188 A | 10/1990 | Mullis et al. |
| 5,066,580 A | 11/1991 | Lee |
| 5,091,519 A | 2/1992 | Cruickshank |
| 5,151,507 A | 9/1992 | Hobbs et al. |
| 5,188,934 A | 2/1993 | Menchen |
| 5,198,537 A | 3/1993 | Huber et al. |
| 5,344,757 A | 9/1994 | Holtke et al. |
| 5,354,657 A | 10/1994 | Boehringer et al. |
| 5,366,860 A | 11/1994 | Bergot et al. |
| 5,512,462 A | 4/1996 | Cheng |
| 5,599,675 A | 2/1997 | Brenner |
| 5,635,352 A | 6/1997 | Urdea et al. |
| 5,688,648 A | 11/1997 | Mathies |
| 5,695,940 A | 12/1997 | Drmanac et al. |
| 5,702,888 A | 12/1997 | Holtke et al. |
| 5,750,341 A | 5/1998 | Macevicz |
| 5,800,996 A | 9/1998 | Lee et al. |
| 5,847,162 A | 12/1998 | Lee et al. |
| 5,969,119 A | 10/1999 | Macevicz |
| 5,990,479 A | 11/1999 | Weiss et al. |
| 6,054,274 A | 4/2000 | Sampson et al. |
| 6,172,218 B1 | 1/2001 | Brenner |
| 6,207,392 B1 | 3/2001 | Weiss et al. |
| 6,251,303 B1 | 6/2001 | Bawendi et al. |
| 6,265,552 B1 | 7/2001 | Schatz |
| 6,291,187 B1 | 9/2001 | Kingsmore et al. |
| 6,306,597 B1 | 10/2001 | Macevicz |
| 6,319,426 B1 | 11/2001 | Bawendi et al. |
| 6,322,901 B1 | 11/2001 | Bawendi et al. |
| 6,323,009 B1 | 11/2001 | Lasken et al. |
| 6,344,329 B1 | 2/2002 | Lizardi et al. |
| 6,368,801 B1 | 4/2002 | Faruqi |
| 6,391,937 B1 | 5/2002 | Beuhler et al. |
| 6,423,551 B1 | 7/2002 | Weiss et al. |
| 6,426,513 B1 | 7/2002 | Bawendi et al. |
| 6,444,143 B2 | 9/2002 | Bawendi et al. |
| 6,534,266 B1 | 3/2003 | Singer |
| 6,576,291 B2 | 6/2003 | Bawendi et al. |
| 6,828,109 B2 | 12/2004 | Kaplan et al. |

(Continued)

FOREIGN PATENT DOCUMENTS

| | | |
|---|---|---|
| WO | WO 1991/017160 | 11/1991 |
| WO | WO 2017/143155 | 8/2017 |

(Continued)

OTHER PUBLICATIONS

Nilsson (Molecular Diagnostics (2010) pp. 117-130).*
Conse (Annu. Rev. Anal. Chem. 2009. 2:215-39).*
Krzywkowski (Imre Gaspar (ed.), RNA Detection: Methods and Protocols, Methods in Molecular Biology, vol. 1649, DOI 10.1007/978-1-4939-7213-5_14, © Springer Science+Business Media LLC 2018).*
Archer et al., "Selective and flexible depletion of problematic sequences from RNA-seq libraries at the cDNA stage," BMC Genomics. (2014) 15(1):401.
Arnaud-Barbe et al., "Transcription of RNA templates by T7 Rna polymerase," Nucleic Acids Res. (1998) 26(15):3550-4.
Baner et al., "Signal amplification of padlock probes by rolling circle replication," Nucleic Acids Res. (1998) 26(22):5073-5078.
Bibikova et al., "Quantitative gene expression profiling in formalin-fixed, paraffin-embedded tissues using universal bead arrays," Am J Pathol. Nov. 2004; 165(5):1799-807.
Bolognesi et al., "Multiplex Staining by Sequential Immunostaining and Antibody Removal on Routine Tissue Sections," J. Histochem. Cytochem. (2017); 65(8): 431-444.

(Continued)

*Primary Examiner* — Steven Pohnert
(74) *Attorney, Agent, or Firm* — MORRISON & FOERSTER LLP

(57) ABSTRACT

The present disclosure relates in some aspects to methods and compositions for analysis of a target nucleic acid, such as in situ detection of a region of interest in a polynucleotide in a tissue sample. In some embodiments, provided herein are templated ligation probes (e.g., RNA-templated ligation probes) and selector probes for generation of a circularized ligated probe comprising an insertion sequence of a selector probe, wherein the circularized ligated probe is amplified in a rolling circle amplification reaction to generate a product that is detected in the sample.

18 Claims, 6 Drawing Sheets

(56) References Cited

U.S. PATENT DOCUMENTS

| | | |
|---|---|---|
| 6,969,488 B2 | 11/2005 | Bridgham et al. |
| 7,057,026 B2 | 6/2006 | Barnes et al. |
| 7,255,994 B2 | 8/2007 | Lao |
| 7,473,767 B2 | 1/2009 | Dimitrov |
| 7,534,991 B2 | 5/2009 | Miller et al. |
| 7,555,155 B2 | 6/2009 | Levenson et al. |
| 7,632,641 B2 | 12/2009 | Dirks et al. |
| 7,655,898 B2 | 2/2010 | Miller |
| 7,721,721 B1 | 5/2010 | Kronengold et al. |
| 7,906,285 B2 | 3/2011 | Drmanac |
| 7,910,304 B2 | 3/2011 | Drmanac |
| 7,941,279 B2 | 5/2011 | Hwang et al. |
| 7,989,166 B2 | 8/2011 | Koch et al. |
| 8,124,751 B2 | 2/2012 | Pierce et al. |
| 8,199,999 B2 | 6/2012 | Hoyt et al. |
| 8,268,554 B2 | 9/2012 | Schallmeiner |
| 8,330,087 B2 | 12/2012 | Domenicali |
| 8,415,102 B2 | 4/2013 | Geiss et al. |
| 8,431,691 B2 | 4/2013 | McKernan et al. |
| 8,460,865 B2 | 6/2013 | Chee et al. |
| 8,462,981 B2 | 6/2013 | Determan et al. |
| 8,481,258 B2 | 7/2013 | Church et al. |
| 8,519,115 B2 | 8/2013 | Webster et al. |
| 8,551,710 B2 | 10/2013 | Bernitz et al. |
| 8,658,361 B2 | 2/2014 | Wu et al. |
| 8,771,950 B2 | 7/2014 | Church et al. |
| 8,986,926 B2 | 3/2015 | Ferree et al. |
| 9,201,063 B2 | 12/2015 | Sood et al. |
| 9,217,178 B2 | 12/2015 | Fedurco et al. |
| 9,273,349 B2 | 3/2016 | Nguyen et al. |
| 9,371,563 B2 | 6/2016 | Geiss et al. |
| 9,371,598 B2 | 6/2016 | Chee |
| 9,376,717 B2 | 6/2016 | Gao et al. |
| 9,404,155 B2 | 8/2016 | Bortner |
| 9,512,422 B2 | 12/2016 | Barnard et al. |
| 9,541,504 B2 | 1/2017 | Hoyt |
| 9,551,032 B2 | 1/2017 | Landegren et al. |
| 9,624,538 B2 | 4/2017 | Church et al. |
| 9,714,446 B2 | 7/2017 | Webster et al. |
| 9,714,937 B2 | 7/2017 | Dunaway |
| 9,727,810 B2 | 8/2017 | Fodor et al. |
| 9,778,155 B2 | 10/2017 | Gradinaru et al. |
| 9,783,841 B2 | 10/2017 | Nolan et al. |
| 9,889,422 B2 | 2/2018 | Smith et al. |
| 9,909,167 B2 | 3/2018 | Samusik et al. |
| 10,032,064 B2 | 7/2018 | Hoyt |
| 10,059,990 B2 | 8/2018 | Boyden et al. |
| 10,126,242 B2 | 11/2018 | Miller et al. |
| 10,138,509 B2 | 11/2018 | Church et al. |
| 10,179,932 B2 | 1/2019 | Church et al. |
| 10,227,639 B2 | 3/2019 | Levner et al. |
| 10,246,700 B2 | 4/2019 | Dunaway et al. |
| 10,266,888 B2 | 4/2019 | Daugharthy et al. |
| 10,267,808 B2 | 4/2019 | Cai |
| 10,309,879 B2 | 6/2019 | Chen et al. |
| 10,317,321 B2 | 6/2019 | Tillberg et al. |
| 10,364,457 B2 | 7/2019 | Wassie et al. |
| 10,370,698 B2 | 8/2019 | Nolan et al. |
| 10,415,080 B2 | 9/2019 | Dunaway et al. |
| 10,457,980 B2 | 10/2019 | Cai et al. |
| 10,465,235 B2 | 11/2019 | Gullberg et al. |
| 10,494,662 B2 | 12/2019 | Church et al. |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,526,649 B2 | 1/2020 | Chen et al. |
| 10,545,075 B2 | 1/2020 | Deisseroth et al. |
| 10,550,429 B2 | 2/2020 | Harada et al. |
| 10,580,128 B2 | 3/2020 | Miller |
| 10,640,816 B2 | 5/2020 | Beechem et al. |
| 10,640,826 B2 | 5/2020 | Church et al. |
| 10,669,569 B2 | 6/2020 | Gullberg et al. |
| 10,746,981 B2 | 8/2020 | Tomer et al. |
| 10,774,372 B2 | 9/2020 | Chee et al. |
| 10,774,374 B2 | 9/2020 | Frisén et al. |
| 10,794,802 B2 | 10/2020 | Gradinaru et al. |
| 10,802,262 B2 | 10/2020 | Tomer et al. |
| 10,815,519 B2 | 10/2020 | Husain et al. |
| 10,829,814 B2 | 11/2020 | Fan et al. |
| 10,844,426 B2 | 11/2020 | Daugharthy et al. |
| 10,858,698 B2 | 12/2020 | Church et al. |
| 10,872,679 B2 | 12/2020 | Cai et al. |
| 10,964,001 B2 | 3/2021 | Miller |
| 11,459,603 B2 | 10/2022 | Tyagi et al. |
| 2002/0045045 A1 | 4/2002 | Adams et al. |
| 2003/0017264 A1 | 1/2003 | Treadway et al. |
| 2005/0100900 A1 | 5/2005 | Kawashima et al. |
| 2006/0188901 A1 | 8/2006 | Barnes et al. |
| 2006/0234261 A1 | 10/2006 | Pierce et al. |
| 2006/0240439 A1 | 10/2006 | Smith et al. |
| 2006/0281109 A1 | 12/2006 | Barr et al. |
| 2007/0166705 A1 | 7/2007 | Milton et al. |
| 2008/0242560 A1* | 10/2008 | Gunderson ............ C12Q 1/682 506/26 |
| 2009/0118128 A1 | 5/2009 | Liu et al. |
| 2010/0055733 A1 | 3/2010 | Lutolf et al. |
| 2011/0059865 A1 | 3/2011 | Smith et al. |
| 2011/0223585 A1 | 9/2011 | Gullberg et al. |
| 2012/0270305 A1 | 10/2012 | Reed et al. |
| 2013/0079232 A1 | 3/2013 | Kain et al. |
| 2013/0260372 A1 | 10/2013 | Buermann et al. |
| 2013/0288249 A1 | 10/2013 | Gullbert |
| 2013/0323729 A1 | 12/2013 | Landegren et al. |
| 2016/0024555 A1 | 1/2016 | Church et al. |
| 2016/0108458 A1 | 4/2016 | Frei et al. |
| 2016/0305856 A1 | 10/2016 | Boyden et al. |
| 2016/0369329 A1 | 12/2016 | Cai et al. |
| 2016/0376642 A1 | 12/2016 | Landegren et al. |
| 2017/0009278 A1 | 1/2017 | Söderberg et al. |
| 2017/0081489 A1 | 3/2017 | Rodriques et al. |
| 2017/0101672 A1 | 4/2017 | Luo et al. |
| 2017/0219465 A1 | 8/2017 | Desseroth et al. |
| 2017/0220733 A1 | 8/2017 | Zhuang et al. |
| 2017/0253918 A1 | 9/2017 | Kohman |
| 2018/0052081 A1 | 2/2018 | Kohman |
| 2018/0080876 A1 | 3/2018 | Rockel et al. |
| 2018/0208967 A1 | 7/2018 | Larman et al. |
| 2018/0237864 A1 | 8/2018 | Imler et al. |
| 2018/0251833 A1 | 9/2018 | Daugharthy et al. |
| 2018/0320226 A1 | 11/2018 | Church et al. |
| 2019/0017106 A1 | 1/2019 | Frisen et al. |
| 2019/0032121 A1 | 1/2019 | Daugharthy et al. |
| 2019/0032128 A1 | 1/2019 | Chen et al. |
| 2019/0055594 A1 | 2/2019 | Samusik et al. |
| 2019/0106733 A1 | 4/2019 | Kishi et al. |
| 2019/0112599 A1 | 4/2019 | Church et al. |
| 2019/0119735 A1 | 4/2019 | Deisseroth et al. |
| 2019/0155835 A1 | 5/2019 | Daugharthy et al. |
| 2019/0161796 A1 | 5/2019 | Hauling et al. |
| 2019/0177718 A1 | 6/2019 | Church et al. |
| 2019/0177800 A1 | 6/2019 | Boutet et al. |
| 2019/0194709 A1 | 6/2019 | Church et al. |
| 2019/0218608 A1 | 7/2019 | Daugharthy et al. |
| 2019/0249248 A1 | 8/2019 | Beechem et al. |
| 2019/0264270 A1 | 8/2019 | Zhuang et al. |
| 2019/0271028 A1 | 9/2019 | Khafizov et al. |
| 2019/0276881 A1 | 9/2019 | Zhuang et al. |
| 2019/0339203 A1 | 11/2019 | Miller et al. |
| 2019/0367969 A1 | 12/2019 | Belhocine |
| 2019/0376956 A1 | 12/2019 | Bobrow et al. |
| 2020/0010891 A1 | 1/2020 | Beechem et al. |
| 2020/0071751 A1 | 3/2020 | Daugharthy et al. |
| 2020/0123597 A1 | 4/2020 | Daniel |
| 2020/0140920 A1 | 5/2020 | Pierce et al. |
| 2020/0224243 A1* | 7/2020 | Desai ................... C12Q 1/682 |
| 2020/0224244 A1 | 7/2020 | Nilsson et al. |
| 2020/0239946 A1 | 7/2020 | Dewal |
| 2020/0354774 A1 | 11/2020 | Church et al. |
| 2020/0354782 A1 | 11/2020 | Dewal |
| 2020/0362398 A1 | 11/2020 | Kishi et al. |
| 2020/0393343 A1 | 12/2020 | Kennedy-Darling et al. |
| 2020/0399689 A1 | 12/2020 | Luo et al. |
| 2021/0017587 A1 | 1/2021 | Cai et al. |

(56) References Cited

U.S. PATENT DOCUMENTS

| | | |
|---|---|---|
| 2021/0115504 A1 | 4/2021 | Cai et al. |
| 2021/0164039 A1 | 6/2021 | Wang et al. |
| 2021/0222234 A1 | 7/2021 | Carlson |
| 2021/0238662 A1 | 8/2021 | Bava |
| 2021/0238674 A1 | 8/2021 | Bava |
| 2021/0254140 A1 | 8/2021 | Stahl et al. |
| 2021/0262018 A1 | 8/2021 | Bava et al. |
| 2021/0277460 A1 | 9/2021 | Bava |
| 2021/0340618 A1 | 11/2021 | Kuhnemund et al. |
| 2021/0340621 A1 | 11/2021 | Daugharthy et al. |
| 2021/0388423 A1 | 12/2021 | Bava et al. |
| 2021/0388424 A1 | 12/2021 | Bava |
| 2022/0010358 A1 | 1/2022 | Kuhnemund et al. |
| 2022/0026433 A1 | 1/2022 | Guo et al. |
| 2022/0042090 A1 | 2/2022 | Lee et al. |
| 2022/0049302 A1 | 2/2022 | Daugharthy et al. |
| 2022/0049303 A1 | 2/2022 | Busby et al. |
| 2022/0083832 A1 | 3/2022 | Shah |
| 2022/0084628 A1 | 3/2022 | Shah |
| 2022/0084629 A1 | 3/2022 | Shah |
| 2022/0128565 A1 | 4/2022 | Miller et al. |
| 2022/0136049 A1 | 5/2022 | Bava et al. |
| 2022/0186300 A1 | 6/2022 | Bava |
| 2022/0195498 A1 | 6/2022 | Kuhnemund et al. |
| 2022/0213529 A1 | 7/2022 | Kuhnemund et al. |
| 2022/0228200 A1 | 7/2022 | Bava |

FOREIGN PATENT DOCUMENTS

| | | |
|---|---|---|
| WO | WO 2018/026873 | 2/2018 |
| WO | WO 2019/199579 | 10/2019 |
| WO | WO 2020/076976 | 4/2020 |
| WO | WO 2020/076979 | 4/2020 |
| WO | WO 2020/096687 | 5/2020 |
| WO | WO 2020/099640 | 5/2020 |
| WO | WO 2020/117914 | 6/2020 |
| WO | WO 2020/123316 | 6/2020 |
| WO | WO 2020/123742 | 6/2020 |
| WO | WO 2020/142490 | 7/2020 |
| WO | WO 2020/240025 | 12/2020 |
| WO | WO 2020/254519 | 12/2020 |
| WO | WO 2021/123282 | 6/2021 |
| WO | WO 2021/123286 | 6/2021 |
| WO | WO 2021/138676 | 7/2021 |
| WO | WO 2021/155063 | 8/2021 |
| WO | WO 2021/168326 | 8/2021 |

OTHER PUBLICATIONS

Capodieci et al., "Gene expression profiling in single cells within tissue," Nat Methods. (2005) 2(9): 663-5.

Chemeris et al., "Real-time hybridization chain reaction," Dokl Biochem Biophys. (2008) 419: 53-55.

Chen et al., "Nanoscale imaging of RNA with expansion microscopy," Nat Methods. (2016) 13:679-684.

Chen et al., "RNA imaging. Spatially resolved, highly multiplexed RNA profiling in single cells," Science. (2015) 348(6233): aaa6090. 16 pgs.

Chen et al., "Expansion Microscopy," Science (2015) 347(6221):543-548.

Choi et al., "Programmable in situ amplification for multiplexed imaging of mRNA expression," Nat Biotechnol. (2010) 28(11): 1208-1212.

Conze et al., "Single molecule analysis of combinatorial splicing," Nucleic Acids Res. (2010) 38(16): e163.

Dean et al., "Rapid Amplification of Plasmid and Phage DNA Using Phi29 DNA Polymerase and Multiply-Primed Rolling Circle Amplification," Genome Research (2001) 11:1095-1099.

Dirks et al., "Triggered amplification by hybridization chain reaction," Proc Natl Acad Sci USA. (2004) 101(43): 15275-15278.

Eng et al., "Transcriptome-scale super-resolved imaging in tissues by RNA seqFISH," Nature. (2019) 568(7751): 235-239.

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.

Faruqi et al., "High-throughput genotyping of single nucleotide polymorphisms with rolling circle amplification," BMC Genomics. (2001) 2:4.

Femino et al., "Visualization of single RNA transcripts in situ," Science. (1998) 280(5363): 585-90.

Forcucci et al., "All-plastic miniature fluorescence microscope for point-of-care readout of bead-based bioassays," J Biomed Opt. (2015) 20(10): 105010.

Gavrilovic et al., "Automated classification of multicolored rolling circle products in dual-channel wide-field fluorescence microscopy," Cytometry A. (2011) 79(7): 518-27.

Geiss et al., "Direct multiplexed measurement of gene expression with color-coded probe pairs," Nat Biotechnol. (2008) 26(3): 317-25.

Glass et al., "SIMPLE: a sequential immunoperoxidase labeling and erasing method," J Histochem Cytochem. (2009) 57(10); 899-905.

Goh, J.J.L. et al. (Jul. 2020, e-pub. Jun. 15, 2020). "Highly Specific Multiplexed RNA Imaging in Tissues With Split-FISH," Nat Methods 17(7):689-693. doi: 10.1038/s41592-020-0858-0. Epub Jun. 15, 2020.

Goransson et al., "A single molecule array for digital targeted molecular analyses," Nucleic Acids Res. 2009 37(1):e7. doi: 10.1093/nar/gkn921.

Gunderson et al. "Decoding randomly ordered DNA arrays." Genome research 14.5 (2004): 870-877.

Gyllborg et al., "Hybridization-based in situ sequencing (HybISS) for spatially resolved transcriptomics in human and mouse brain tissue," Nucleic Acids Res. (2020) 48(19): e112.

HaloPlex Target Enrichment System Manual, Agilent Technologies, Jul. 2018; 54 pages.

Han et al., "Quantum-dot-tagged microbeads for multiplexed optical coding of biomolecules," Nat Biotechnol. (2001) 19(7): 631-5.

Henegariu et al., "Custom fluorescent-nucleotide synthesis as an alternative method for nucleic acid labeling," Nature Biotechnol. (2000) 18:345.

Itzkovitz et al., "Single-molecule transcript counting of stem-cell markers in the mouse intestine," Nat Cell Biol. (2011) 14(1): 106-14.

Itzkovitz et al., "Validating Transcripts with Probes and Imaging Technology," Nat Methods. (2011) 8(4 Suppl): S12-S19.

Jamur et al., "Permeabilization of cell membranes," Method Mol. Biol. (2010) 588: 63-66 (abstract only).

Korlach et al. "Selective aluminum passivation for targeted immobilization of single DNA polymerase molecules in zero-mode waveguide nanostructures." *Proceedings of the National Academy of Sciences* 105.4 (2008): 1176-1181.

Lagunavicius et al., "Novel application of Phi29 DNA polymerase: RNA detection and analysis in vitro and in situ by target RNA-primed RCA," RNA. (2009) 15(5):765-71.

Lakowicz et al., "Silver particles enhance emission of fluorescent DNA oligomers," Bio Techniques (2003) 34(1); 62-66.

Larsson et al. "In situ detection and genotyping of individual mRNA molecules," Nat Methods. (2010) 7(5):395-397.

Lee et al. "Highly Multiplexed Subcellular RNA Sequencing In Situ", Science (2014) 343(6177):1360-1363.

Levene et al. "Zero-mode waveguides for single-molecule analysis at high concentrations." *science* 299.5607 (2003): 682-686.

Levsky et al., "Fluorescence in situ hybridization: past, present and future," J Cell Sci. (2003) 116(Pt 14): 2833-8.

Levsky et al., "Single-cell gene expression profiling," Science. (2002) 297(5582): 836-40.

Lin et al., "Highly multiplexed imaging of single cells using a high-throughput cyclic immunofluorescence method," Nat Commun. (2015) 6:8390.

Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.

Lizardi et al., "Mutation detection and single-molecule counting using isothermal rolling-circle amplification," Nat Genet. (1998) 19(3): 225-232.

(56) References Cited

OTHER PUBLICATIONS

Lundquist et al. "Parallel confocal detection of single molecules in real time." Optics letters 33.9 (2008): 1026-1028.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Mohsen et al., "The Discovery of Rolling Circle Amplification and Rolling Circle Transcription," Acc Chem Res. (2016) 49(11): 2540-2550.
Niu et al., "Fluorescence detection for DNA using hybridization chain reaction with enzyme-amplification," Chem Commun (Camb). (2010) 46(18): 3089-91.
Payne et al. "In situ genome sequencing resolves DNA sequence and structure in intact biological samples," Science. (2021) 371(6532): eaay3446. doi: 10.1126/science.aay3446. Epub Dec. 31, 2020.
Petkovic et al., "RNA circularization strategies in vivo and in vitro," Nucleic Acids Res. (2015) 43(4):2454-65.
Pirici et al., "Antibody elution method for multiple immunohistochemistry on primary antibodies raised in the same species and of the same subtype," J Histochem Cytochem. (2009) 57(6); 567-75.
Raj et al., "Imaging individual mRNA molecules using multiple singly labeled probes," Nat Methods. (2008) 5(10): 877-879.
Rajeswari et al., "Multiple pathogen biomarker detection using an encoded bead array in droplet PCR," J Microbiol Methods. (2017) 139: 22-28.
Rouhanifard et al. "ClampFISH detects individual nucleic acid molecules using click chemistry-based amplification," Nat Biotechnol. (2018) 17 pages. doi: 10.1038/nbt.4286.
Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech. (2002) 20:359-365.
Shendure et al., "Accurate multiplex polony sequencing of an evolved bacterial genome," Science (2005) 309(5741); 1728-1732.
Song et al., "Hybridization chain reaction-based aptameric system for the highly selective and sensitive detection of protein," Analyst. (2012) 137(6):1396-1401.
Sun et al., "Composite organic-inorganic nanoparticles as Raman labels for tissue analysis," Nano Lett. (2007) 7(2): 351-6.
Takei et al., (Feb. 2021, e-pub Jan. 27, 2021). "Integrated Spatial Genomics Reveals Global Architecture of Single Nuclei," Nature 590(7845):344-350, 53 pages. doi: 10.1038/s41586-020-03126-2.
Vandernoot et al., "cDNA normalization by hydroxyapatite chromatography to enrich transcriptome diversity in RNA-seq applications," Biotechniques, (2012) 53(6) 373-80.
Wählby et al., "Sequential immunofluorescence staining and image analysis for detection of large numbers of antigens in individual cell nuclei," Cytometry. (2002) 47(1): 32-41.
Wang et al., "Three-dimensional intact-tissue sequencing of single-cell transcriptional states," Science. (2018) 361(6400): eaat5691.
Weibrecht et al., "Simultaneous visualization of both signaling cascade activity and end-point gene expression in single cells," PLoS One. (2011) 6(5): e20148.
Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu, C. et al. "RollFISH Achieves Robust Quantification of Single-Molecule RNA Biomarkers in Paraffin-Embedded Tumor Tissue Samples," Commun Biol. (2018) 1:(209):1-8. doi: 10.1038/s42003-018-0218-0.
Xia et al. "Multiplexed detection of RNA using MERFISH and branched DNA amplification." Scientific reports 9.1 (2019): 1-13.
Xiong et al., "Stepwise "Click" Chemistry for the Template Independent Construction of a Broad Variety of Cross-Linked Oligonucleotides: Influence of Linker Length, Position, and Linking Number on DNA Duplex Stability," J. Org. Chem. (2011) 76(14): 5584-5597.
Zhao et al., "Advances of multiplex and high throughput biomolecular detection technologies based on encoding microparticles," Sci China Chem. (2011) 54(8):1185.
Zhou et al., "A Programmable DNA Ring/Hairpin-Constrained Structure Enables Ligation-Free Rolling Circle Amplification for Imaging mRNAs in Single Cells," Anal, Chem. (2019) 91; 3628-3635.

\* cited by examiner

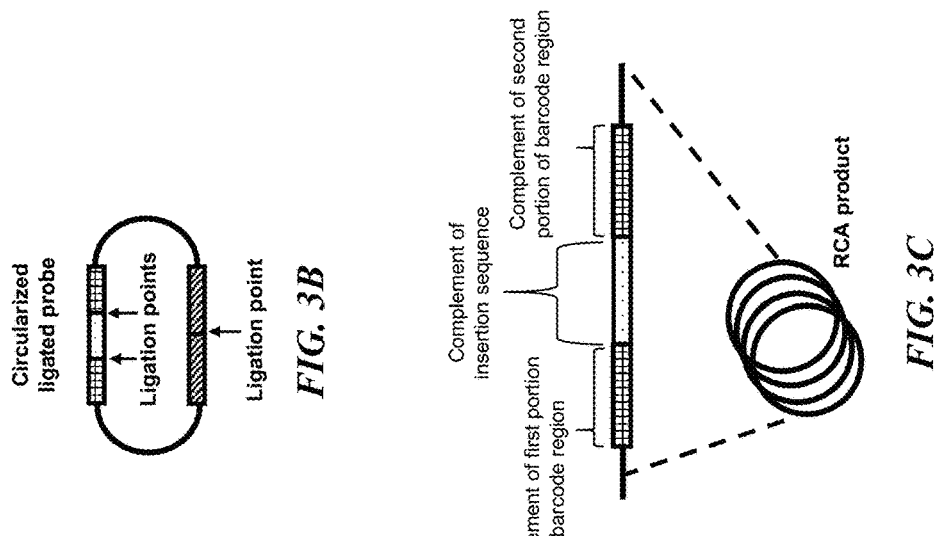
FIG. 3B
FIG. 3C
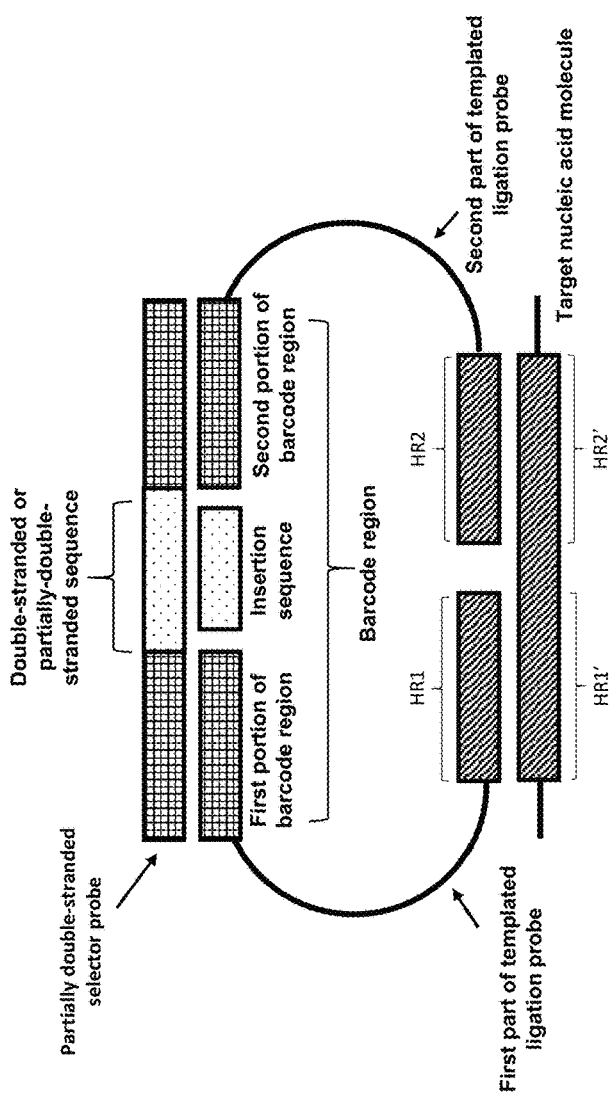
FIG. 3A

CIRCULARIZABLE PROBES FOR IN SITU ANALYSIS

CROSS-REFERENCE TO RELATED APPLICATIONS

This application claims priority to U.S. Provisional Patent Application No. 63/227,829, filed Jul. 30, 2021, entitled "CIRCULARIZABLE PROBES FOR IN SITU ANALYSIS," which is herein incorporated by reference in its entirety for all purposes. This application claims priority to U.S. Provisional Patent Application No. 63/277,106, filed Nov. 8, 2021, entitled "CIRCULARIZABLE PROBES FOR IN SITU ANALYSIS," which is herein incorporated by reference in its entirety for all purposes.

FIELD

The present disclosure relates in some aspects to methods and compositions for analysis of a target nucleic acid, such as in situ detection of a region of interest in a polynucleotide in a tissue sample.

BACKGROUND

Methods are available for analyzing nucleic acids present in a biological sample, such as a cell or a tissue. For instance, advances in single molecule fluorescent in situ hybridization (smFISH) have enabled nanoscale-resolution imaging of RNA in cells and tissues. However, improving low assay specificity and/or stringency and reducing high rates of false positive results remains challenging. In some cases, methods that require a ligation step templated by a target nucleic acid are limited by the specificity and/or efficiency of the templated ligation step. Furthermore, length limits of oligonucleotide synthesis limit the production of probes containing higher numbers of barcode sequences. Thus, improved methods for analyzing nucleic acids present in a biological sample are needed. Provided herein are methods and compositions that address such and other needs.

BRIEF SUMMARY

In some aspects, provided herein is a method for analyzing a biological sample, the method comprising: a) contacting the biological sample comprising a target nucleic acid with a templated ligation probe comprising a first part and a second part, wherein at least one of the first part and the second part comprises a target specific binding site which is complementary to a cognate probe-binding site at or adjacent to a region of interest in the target nucleic acid, wherein the first part and the second part hybridize to the target nucleic acid such that ligatable ends of the first and second parts are juxtaposed for ligation to each other using the target nucleic acid as a ligation template; b) ligating the first and second parts using the target nucleic acid as a template, thereby generating a ligated probe; c) contacting the biological sample with a selector probe comprising a first strand and a second strand that form a partially double stranded probe, wherein the first strand comprises a first homology arm complementary to a first end of the ligated probe, a second homology arm complementary to a second end of the ligated probe, and a region that hybridizes to the second strand, and wherein the second strand comprises an insertion sequence; d) circularizing the ligated probe using the selector probe as a template, thereby generating a circularized ligated probe comprising the insertion sequence from a double stranded or partially double-stranded region of the selector probe; e) performing rolling circle amplification of the circularized ligated probe in the biological sample to generate a rolling circle amplification product; and f) detecting the rolling circle amplification product in the biological sample. In some embodiments, the rolling circle amplification of the circularized ligated probe can be performed using a sequence of the double stranded region of the selector probe as a primer for the rolling circle amplification.

In any of the preceding embodiments, the rolling circle amplification of the circularized ligated probe can be performed using a sequence of the first and/or second homology arm as a primer.

In any of the preceding embodiments, the rolling circle amplification of the circularized ligated probe can be performed using the first strand of the selector probe as a primer.

In any of the preceding embodiments, the first strand of the selector probe can be longer than the second strand of the selector probe, and the first strand hybridizes to the second strand. In some embodiments, the first and second homology arms are single stranded sequences on either side of the double stranded region of the selector probe.

In any of the preceding embodiments, the selector can function to circularize RNA.

In some embodiments, the selector probe can be an RNA-DNA hybrid. In some embodiments, the first strand of the selector probe can comprise DNA and the second strand of the selector probe comprises RNA.

In any of the preceding embodiments, the region of the selector probe comprising the insertion sequence is a double-stranded region of the selector probe.

In any of the preceding embodiments, the region of the selector probe comprising the insertion sequence can be a partially double-stranded region of the selector probe, optionally wherein a portion of the insertion sequence does not hybridize to the first strand of the selector probe. In some embodiments, the portion of the insertion sequence that does not hybridize to the selector probe forms a loop between the ends of the insertion sequence.

In any of the preceding embodiments, the insertion sequence can comprise an insertion barcode sequence and/or a common sequence.

In any of the preceding embodiments, the ligating in b) can be performed after a gap filling step using the target nucleic acid as a template.

In any of the preceding embodiments, the first part and the second part can hybridize to the target nucleic acid such that ligatable ends of the first and second parts are juxtaposed for ligation to create one or more ligation sites at or adjacent to the region of interest In any of the preceding embodiments, in the circularizing step, the insertion sequence can be ligated to both ends of the ligated probe.

In any of the preceding embodiments, the first part and/or the second part can each comprise an overhang that does not hybridize to the target nucleic acid. In some embodiments, the overhang is or comprises an adapter region. In some embodiments, an adapter region herein hybridizes to a homology arm of the selector probe. In some embodiments, the adapter region is a common adapter region. Alternatively, in some embodiments, the adapter region corresponds to a sequence of the target nucleic acid. In some embodiments, the adapter region is or comprises a barcode sequence or a portion of a barcode region.

In any of the preceding embodiments, the first part can comprise an overhang comprising a first portion of a barcode region and the second part can comprise an overhang comprising a second portion of the barcode region, wherein the barcode region comprises one or more barcode sequences. In some embodiments, the first portion of the barcode region can be located at an end of the first part and the second portion of the barcode region can be located at an end of the second part. In some embodiments, the first homology arm of the selector probe can be complementary to all or part of the first portion of the barcode region and the second homology arm of the selector probe can be complementary to all or part of the second portion of the barcode region.

In any of the preceding embodiments, the overhang can further comprise one or more overhang barcode sequences, optionally wherein the one or more barcode sequences correspond to a sequence of the target nucleic acid.

In any of the preceding embodiments, the insertion barcode sequence, the one or more overhang barcode sequences, and/or one or more barcode sequences of the barcode region each is independently between about 5 and about 35 nucleotides in length. In some embodiments, the one or more barcode sequences each is independently between about 10 and about 20 nucleotides in length.

In any of the preceding embodiments, the first portion of the barcode region can comprise one, two, or more barcode sequences and/or the second portion of the barcode region can comprise one, two, or more barcode sequences. In some embodiments, the barcode region can comprise two or more adjacent barcode sequences. In some embodiments, the barcode region can comprise two or more non-overlapping barcode sequences and/or two or more overlapping barcode sequences.

In any of the preceding embodiments, the selector probe can hybridize to the ligated probe more stably when the selector probe comprises complementary sequences to both (i) an adapter region of the first part and (ii) an adapter region of the second part, as compared to when the selector probe comprises a mismatch with (i) the adapter region of the first part and/or (ii) the adapter region of the second part. In some embodiments, the method can comprise removing the selector probe comprising a mismatch with (i) the adapter region of the first part and/or (ii) the adapter region of the second part, whereas under the same conditions, the selector probe complementary to both (i) the adapter region of the first part and (ii) the adapter region of the second part remains hybridized to the adapter regions of the first part and second part for subsequent ligation.

In any of the preceding embodiments, the selector probe can hybridize to the barcode region more stably when the selector probe comprises complementary sequences to both (i) the first portion or a subportion thereof and (ii) the second portion or a subportion thereof, as compared to when the selector probe comprises a mismatch with (i) the first portion or a subportion thereof and/or (ii) the second portion or a subportion thereof. In some embodiments, the method comprises removing the selector probe comprising a mismatch with (i) the first portion or a subportion thereof and/or (ii) the second portion or a subportion thereof, whereas under the same conditions, the selector probe complementary to both (i) the first portion or a subportion thereof and (ii) the second portion or a subportion thereof remains hybridized to the barcode region for subsequent ligation.

In any of the preceding embodiments, the melting temperature of the first portion or subportion thereof hybridized to the selector probe can equal the melting temperature of the second portion or subportion thereof hybridized to the selector probe. Alternatively, in any of the preceding embodiments, the melting temperature of the first portion or subportion thereof hybridized to the selector probe can be higher or lower than the melting temperature of the second portion or subportion thereof hybridized to the selector probe. In some embodiments, the melting temperatures differ by no more than 1° C., no more than 2° C., no more than 5° C., or no more than 10° C. Alternatively, in some embodiments the melting temperatures can differ by 1° C. or more, 2° C. or more, 5° C. or more, or 10° C. or more.

In any of the preceding embodiments, the overhang can further comprise one or more barcode sequences corresponding to a sequence of the target nucleic acid.

In any of the preceding embodiments, the selector probe can be immobilized in the biological sample and/or a matrix embedding the biological sample. In some embodiments, the selector probe is immobilized at its 5' end and is used as a primer to generate the rolling circle amplification product of the circularized ligated probe.

In any of the preceding embodiments, the target nucleic acid can comprise RNA. In some embodiments, the target nucleic acid is an mRNA.

In any of the preceding embodiments, the first and/or second part may not comprise an overhang region. In some embodiments, the first and/or second part can be fully hybridized to the target nucleic acid. In some embodiments, the first and second parts do not comprise overhang regions, and the insertion sequence comprises a barcode sequence.

In any of the preceding embodiments, the method can further comprise releasing the probe from the target nucleic acid. In some embodiments, the releasing can comprise RNase H digestion of the target nucleic acid.

In any of the preceding embodiments, the target nucleic acid can comprise DNA.

In some aspects, provided herein is a method for analyzing a biological sample, the method comprising: a) contacting the biological sample comprising a target RNA with a templated ligation probe comprising a first part and a second part, wherein at least one of the first part and the second part comprises a target specific binding site which is complementary to a cognate probe-binding site at or adjacent to a region of interest in the target RNA, wherein the first part and the second part hybridize to the target RNA such that, optionally after a gap filling step using the target RNA as a template, ligatable ends of the first and second parts are juxtaposed for ligation to each other using the target RNA as a ligation template, to create one or more ligation sites at or adjacent to the region of interest; b) ligating the first and second parts using the target RNA as a template, thereby generating a ligated probe; c) releasing the ligated probe from the target RNA; d) contacting the biological sample with a selector probe comprising a first strand and a second strand that form a partially double stranded probe, wherein the first strand comprises a first homology arm complementary to a first end of the ligated probe, a second homology arm complementary to a second end of the ligated probe, and a region that hybridizes to the second strand, and wherein the second strand comprises an insertion sequence; e) circularizing the ligated probe using the selector probe as a template; and f) detecting a rolling circle amplification product of the circularized ligated probe in the biological sample.

In some embodiments, the releasing step can comprise RNAse H digestion of the target RNA.

In any of the preceding embodiments, the insertion sequence can comprise one or more insertion barcode sequences.

In any of the preceding embodiments, the insertion sequence can comprise an anchor binding sequence or a complement thereof.

In any of the preceding embodiments, the first part and/or the second part may not comprise an overhang region. In some embodiments, the first and/or second part is fully hybridized to the target nucleic acid.

In any of the preceding embodiments, the rolling circle amplification product can comprise multiple copies of a sequence complementary to the circularized ligated probe, wherein the sequence complementary to the circularized ligated probe comprises the complement of the insertion sequence.

In some embodiments, the sequence complementary to the circularized ligated probe comprises the complement of the insertion barcode sequence, the one or more overhang barcode sequences, and/or the one or more barcode sequences of the barcode region. In some embodiments, the sequence complementary to the circularized ligated probe can comprise the complement of a first portion of a barcode region and the complement of a second portion of the barcode region flanking the complement of the insertion sequence.

In any of the preceding embodiments, the detecting can comprise detecting a sequence in the sequence complementary to the circularized ligated probe. In some embodiments, the detecting comprises sequencing all or a portion of the sequence complementary to the circularized ligated probe and/or in situ hybridization to the sequence complementary to the circularized ligated probe. In some embodiments, the detecting comprises sequencing the complements of one or more barcode sequences (e.g., the complements of one or more insertion barcode sequences, one or more overhang barcode sequences, and/or one or more barcode sequences comprised by the barcode region comprising a first portion and a second portion). In some embodiments, the detecting can comprise sequencing the complement of the first portion of the barcode region and the complement of the second portion of the barcode region flanking the complement of the insertion sequence. In any of the preceding embodiments, the detecting can comprise sequencing all or a portion of the complement of the target specific binding site of the first and/or second part.

In any of the preceding embodiments, the detecting can comprise: contacting the biological sample with one or more detectably-labeled probes that directly or indirectly bind to the one or more barcode sequences or complements thereof, detecting signals associated with the one or more detectably-labeled probes, and removing the one or more detectably-labeled probe. In any of the preceding embodiments, the detecting can comprise: contacting the biological sample with one or more intermediate probes that directly or indirectly bind to the one or more barcode sequences or complements thereof, wherein the one or more intermediate probes are detectable using one or more detectably-labeled probes, and detecting signals associated with the one or more detectably-labeled probes. In any of the preceding embodiments, the method can further comprise removing the one or more intermediate probes and/or the one or more detectably-labeled probes.

In some aspects, provided herein is a method for analyzing a biological sample, the method comprising: a) contacting the biological sample comprising a target RNA with a first probe and a second probe, wherein the first probe and the second probe each comprises a target specific binding site which is complementary to a cognate probe-binding site at or adjacent to a region of interest in the target RNA; b) releasing the region of interest from the target RNA; c) contacting the biological sample with a selector probe comprising a first strand and a second strand that form a partially double stranded probe, wherein the first strand comprises a first homology arm complementary to a first end of the released region of interest, a second homology arm complementary to a second end of the released region of interest, and a region that hybridizes to the second strand, and wherein the second strand comprises an insertion sequence; d) circularizing the region of interest using the selector probe as a template; and e) detecting the circularized region of interest in the biological sample. In some embodiments, the releasing comprises enzymatic digestion of the target RNA. In some embodiments, the enzymatic digestion comprises RNAse H digestion. In some embodiments, the first probe and second probe are DNA probes. In some embodiments, the insertion sequence comprises one or more insertion barcode sequences. In some embodiments, the insertion sequence comprises an anchor sequence. In some embodiments, the first probe and/or the second probe does not comprise an overhang region. In some embodiments, the first probe and/or the second probe is fully hybridized to the target nucleic acid.

In any of the preceding embodiments, the rolling circle amplification product can comprise multiple copies of a sequence complementary to the circularized ligated probe, wherein the sequence complementary to the circularized region of interest comprises the complement of the insertion sequence.

In any of the preceding embodiments, the detecting can comprise detecting a sequence in the sequence complementary to the circularized region of interest. In some embodiments, the detecting comprises sequencing all or a portion of the sequence complementary to the circularized region of interest and/or in situ hybridization to the sequence complementary to the circularized region of interest. In some embodiments, the detecting comprises sequencing the complement of the insertion barcode sequence.

In any of the preceding embodiments, the sequencing can comprise sequencing by hybridization (SBH), sequencing by ligation (SBL), and/or fluorescent in situ sequencing.

In any of the preceding embodiments, the sequencing by hybridization can comprise sequential fluorescent in situ hybridization.

In any of the preceding embodiments, the sequencing by ligation can comprise hybridizing a sequencing primer to the complement of the insertion sequence. In some embodiments, the sequencing by ligation can comprise contacting the sample with a plurality of detection probes, wherein a detection probe complementary to a sequence of interest adjacent to the complement of the insertion sequence is ligated to the sequencing primer. In some embodiments, the method can comprise performing sequencing by ligation to determine a sequence 5' to the complement of the insertion sequence and/or performing sequencing by ligation to determine a sequence 3' to the complement of the insertion sequence. In some embodiments, the sequence 5' to the complement of the insertion sequence is the complement of a first portion of a barcode sequence comprised by the first part of the templated ligation probe, and the sequence 3' to the complement of the insertion sequence is the complement of a second portion of the barcode sequence comprised by the second part of the templated ligation probe. Alternatively, in some embodiments, the sequence 3' to the complement of the insertion is a first portion of a barcode sequence comprised by the first part of the templated ligation probe or a complement thereof, and the sequence 5' to the complement of the insertion sequence is a second portion of the barcode sequence comprised by the second part of the templated ligation probe or a complement thereof.

In any of the preceding embodiments, the detecting can comprise hybridizing to the rolling circle amplification product a detection oligonucleotide labeled with a fluorophore, an isotope, a mass tag, or a combination thereof.

In any of the preceding embodiments, the detecting can comprise imaging the rolling circle amplification product.

In any of the preceding embodiments, the sample can comprise a plurality of target nucleic acids, and the method can comprise: a) contacting the sample with a plurality of templated ligation probes, wherein each templated ligation probe of the plurality comprised a first part and a second part, wherein at least one of the first part and the second part comprises a target specific binding site which is complementary to a cognate probe-binding site at or adjacent to a region of interest in the target nucleic acid, wherein the first part and the second part hybridize to a target nucleic acid of the plurality of target nucleic acids such that ligatable ends of the first and second parts are juxtaposed for ligation to each other using the target nucleic acid as a ligation template; b) for a plurality of templated ligation probes, ligating the first and second parts using the target nucleic acid as a template, thereby generating a plurality of ligated probes; c) contacting the biological sample with a plurality of selector probes, wherein each selector probe of the plurality comprises a first strand and a second strand that form a partially double stranded probe, wherein the first strand comprises a first homology arm complementary to a first end of a cognate ligated probe of the plurality of ligated probes, a second homology arm complementary to a second end of the cognate ligated probe of the plurality of ligated probes, and a region that hybridizes to the second strand, and wherein the second strand comprises an insertion sequence; d) circularizing the ligated probes using their cognate selector probes as templates, thereby generating a plurality of circularized ligated probes comprising the insertion sequence from a double stranded or partially double-stranded region of their cognate selector probes; e) performing rolling circle amplification of the circularized ligated probes in the biological sample to generate a plurality of rolling circle amplification products; and f) detecting the rolling circle amplification products in the biological sample. In some embodiments, a selector probe "cognate" to a given ligated probe is a selector probe comprising homology arms complementary to the ends of said ligated probe. In some embodiments, the selector probe can uniquely correspond to a particular ligated probe, and may thus uniquely correspond to a target sequence of a target nucleic acid. In other embodiments, multiple ligated probes can comprise common adapter regions such that the same selector probe is cognate to multiple ligated probes.

In some embodiments, the insertion sequence of a selector probe cognate to a given ligated probe can comprise an insertion barcode sequence corresponding to the ligated probe. In some embodiments, a plurality of the selector probes cognate to different ligated probes can comprise common insertion sequences. In some embodiments, the common insertion sequences can be common primer binding sequences or complements thereof or common anchor binding sequences or complements thereof.

In any of the preceding embodiments, the method can comprise hybridizing a detection anchor probe to the complement of a common anchor binding sequence comprised by a plurality of the rolling circle amplification products. The detection anchor probe can be detectably labeled as described in Section V (e.g., directly or indirectly labeled with a detectable moiety). In some embodiments, the method can comprise imaging the sample to detect the plurality of rolling circle amplification products simultaneously.

In any of the preceding embodiments, the target nucleic acid can be in a sample, and the detecting can be performed in situ in the sample. In some embodiments, the sample is a fixed and/or permeabilized biological sample. In some embodiments, the sample is a tissue sample. In some embodiments, the sample is a formalin-fixed, paraffin-embedded (FFPE) tissue sample, a frozen tissue sample, or a fresh tissue sample. In some embodiments, the sample is a tissue slice between about 1 μm and about 50 μm in thickness. In some embodiments, the tissue slice is between about 5 μm and about 35 μm in thickness. In some embodiments, the sample is crosslinked. In some embodiments, the sample is embedded in a hydrogel matrix. In some embodiments, the sample is not embedded in a hydrogel matrix. In some embodiments, the sample is cleared.

In some aspects, provided herein is a kit for generating a circularized ligated probe, comprising: (i) a templated ligation probe comprising a first part and a second part, wherein at least one of the first part and the second part comprises a target specific binding site which is complementary to a cognate probe-binding site at or adjacent to a region of interest in a target nucleic acid, wherein the first part and the second part, respectively, comprise a first hybridization region and second hybridization region cognate to a first and second sequence of the target nucleic acid, such that upon hybridization of the first part and second part to the target nucleic acid ligatable ends of the first and second parts are juxtaposed for ligation to each other using the target nucleic acid as a ligation template to generate a ligated probe; and (ii) a selector probe comprising a first strand and a second strand that form a partially double stranded probe, wherein the first strand comprises a first homology arm complementary to a first end of the ligated probe, a second homology arm complementary to a second end of the ligated probe, and a region that hybridizes to the second strand, and wherein the second strand comprises an insertion sequence.

In some embodiments, the first part and the second part each comprise an overhang sequence that does not hybridize to the target nucleic acid. In some embodiments, the overhang comprises an adapter region complementary to a homology arm of the selector probe. In some embodiments, the homology arms of the selector probe hybridize to the adapter regions of the ligated probe. In some embodiments, the adapter region is a common adapter region and optionally the insertion sequence is an anchor or sequencing primer binding sequence or a complement thereof. Alternatively, in some embodiments, the adapter region corresponds to a sequence of the target nucleic acid and optionally the insertion sequence comprises a barcode sequence corresponding to the target nucleic acid.

In any of the preceding embodiments, the first part can comprise a first portion of a barcode region, and the second part can comprise a second portion of the barcode region. In some embodiments, the first portion of the barcode region can be complementary to the first homology arm of the selector probe, and the second portion of the barcode region can be complementary to the second homology arm of the selector probe. In any of the preceding embodiments, the insertion sequence can comprise a third portion of the barcode region, and/or the insertion sequence can comprise a common sequence. In some embodiments, the insertion sequence comprises a common anchor binding sequence or a complement thereof. In some embodiments, the insertion sequence comprises a common primer binding sequence or a complement thereof. In some embodiments, the kit further comprises a detection anchor probe for detecting a plurality of rolling circle amplification products, and/or a sequencing primer for performing a sequencing by ligation reaction.

BRIEF DESCRIPTION OF THE DRAWINGS

The drawings illustrate certain embodiments of the features and advantages of this disclosure. These embodiments are not intended to limit the scope of the appended claims in any manner.

FIGS. 3A-3C show an exemplary set of probes and method described herein, wherein the ligated probe formed from the templated ligation probes comprises a split barcode region. FIG. 3A depicts an exemplary set of probes wherein the overhang region of the first part and the overhang region of the second part of the templated ligation probes comprise a first and second portion of a barcode region, respectively, and the selector probe hybridizes to the first and second portion of the barcode region. FIG. 3B shows a circularized ligated probe formed by ligation of the first and second part of the templated ligation probe using the target nucleic acid molecule as a template, and circularization of the ligated probe by the selector probe, thereby inserting the insertion sequence between the first portion and second portion of the barcode region. FIG. 3C shows an exemplary RCA product generated by rolling circle amplification of the circularized ligated probe, wherein the RCA product comprises multiple copies of a sequence complementary to the first portion of the barcode region, insertion sequence, and second portion of the barcode region.

FIGS. 4A-4B depict an exemplary method of sequencing the complement of the first portion of the barcode region by SBL from a first end of the sequencing primer which hybridizes to the sequencing primer binding sequence, and FIGS. 4C-4D depict an exemplary method of sequencing the complement of the second portion of the barcode region by SBL from a second end of the sequencing primer. The first and/or second portion of the barcode region could be sequenced by SBL in any order.

DETAILED DESCRIPTION

Figure 1:
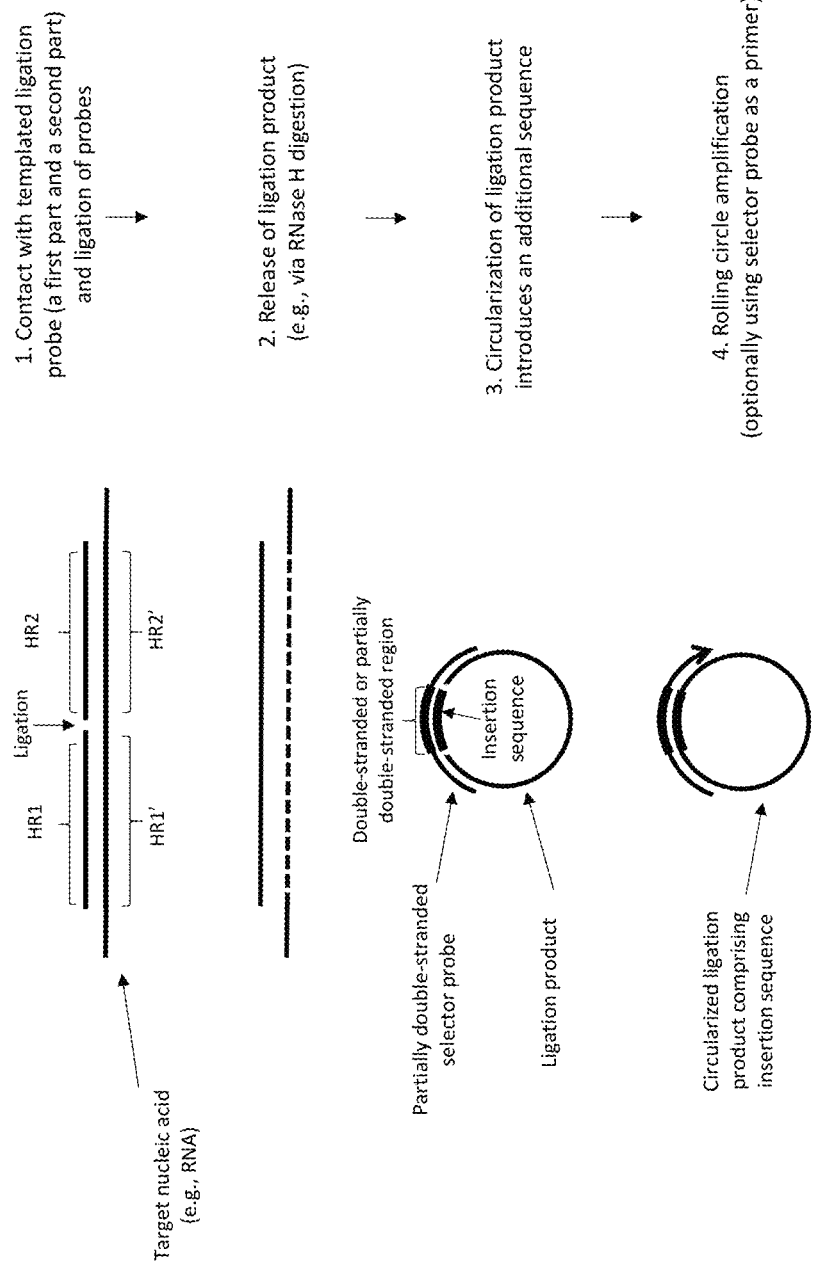
FIG. 1 depicts an exemplary method described herein. The method can comprise contacting a biological sample comprising a target nucleic acid with a templated ligation probe comprising a first part and a second part, wherein the first part and the second part comprise target specific binding sites HR1 and HR2, respectively, which are complementary to a cognate probe-binding sites (HR1' and HR2') at or adjacent to a region of interest in the target nucleic acid. The first part and the second part hybridize to the target nucleic acid such that ligatable ends of the first and second parts are juxtaposed for ligation to each other using the target nucleic acid as a ligation template and can be ligated as in step (1). In some embodiments, the ligation product can be released from the target nucleic acid (e.g., by RNase H digestion of target RNA hybridized to the ligated probe), as shown in (2). The ligated probe can then be circularized using a selector probe comprising a first strand and a second strand that form a partially double stranded probe as shown in (3), thereby generating a circularized ligated probe comprising an insertion sequence from a double stranded or partially double-stranded region of the selector probe. The circularized ligated probe can then be amplified by rolling circle amplification as shown in (4).

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein are methods, compositions, and kits for analyzing a biological sample using templated ligation probes that are circularized with a selector probe, and amplifying the circularized product using RCA.

In some aspects, the methods provided herein comprise ligation of probes at three ligation points to generate a circularized probe. In some embodiments, a templated ligation probe (e.g., an RNA-templated ligation probe) is provided in a first part and a second part that hybridize to adjacent regions of a target nucleic acid and are then ligated in a ligation templated by the target nucleic acid, with or without gap-filling prior to ligation. In some embodiments, the first part and/or second part comprises a target specific binding site (e.g., an interrogatory region) complementary to a cognate probe-binding region (e.g., a region of interest) in the target nucleic acid, such that the ligation of the first and second part depends on the presence of the region of interest in the target nucleic acid. In some embodiments, the first part and second part hybridize completely to the target nucleic acid (e.g., do not comprise any overhangs). In some embodiments, the ligated probe can be released from the target nucleic acid (e.g., by digestion with RNase H), thus freeing the ends of the ligated probe for the second and third ligation. In some embodiments, the first and second part can each comprise an overhang region such that the ligated probe comprises two overhangs that are available for ligating. In some embodiments, the overhangs comprise target-specific sequences (e.g., sequences corresponding to the target sequence and/or region of interest). In some embodiments, the overhangs comprise common sequences (e.g., the same overhangs can be used for multiple different templated ligation probes to insert common sequences into the probes).

In some aspects, the ligated probe is circularized by ligation using a selector probe (e.g., a second and third ligation to insert a sequence into the circularized probe). In some embodiments, a "selector probe" or "selector" is a nucleic acid probe comprising a first strand and a second strand, wherein the first strand and the second strand form a partially double stranded probe. The selector probe comprises one longer strand and one shorter strand. The first strand comprises a first homology arm complementary to a first end of the ligated probe, a second homology arm complementary to a second end of the ligated probe, and a region that hybridizes partially or completely to the second strand. The second strand comprises an insertion sequence (e.g., a common sequence such as an anchor sequence or primer binding sequence or a complement thereof, and/or a sequence corresponding to the target nucleic acid, such as a barcode sequence). The first strand and second strand can independently be DNA, RNA, PNA or any other synthetic nucleic acid derivative. In some embodiments, the region of the selector probe comprising the insertion sequence can be a partially double-stranded region of the selector probe. In some embodiments, a portion of the insertion sequence does not hybridize to the first strand of the selector probe. In some embodiments, the portion of the insertion sequence that does not hybridize to the selector probe forms a loop between the ends of the insertion sequence, thus allowing insertion of a longer insertion sequence.

In some embodiments, the templated ligation probes and selector probes described here address the length limitations of traditional padlock or circular probes because the selector probe can be used to add an insertion sequence (e.g., a common sequence and/or barcode sequence) to the circularized probe, thus overcoming a bottleneck of oligonucleotide synthesis and making it possible to increase the barcoding space/potential within the circular probes.

In some aspects, low specificity and/or sensitivity has been observed when using certain ligases (e.g., SplintR) during the ligation of probes. In some aspects, the present disclosure provides methods and compositions using approaches and probe designs that allow the use of certain ligases (e.g., SplintR) and achieves high specificity and sensitivity. In some embodiments, the templated ligation probes and/or selector probes described herein can be used to provide additional enrichment step.

In some aspects, the use of the selector probe can increase specificity of the method for detecting target nucleic acids by templated ligation by selecting against chimeric ligated probes. For example, in some examples, a chimeric ligated probe (e.g., first part corresponding to target A ligated to second part corresponding to target B) will comprise a sequence at one end of the ligated probe that corresponds to target A and a sequence at the other end of the ligated probe that corresponds to target B. In some embodiments, a selector probe comprising a first and second homology arm corresponding to target A or a first and second homology arm corresponding to target B would fail to circularize the chimeric AB probe (e.g., would only hybridize to a single homology arm and would fail to ligate both ends of the probe). In some aspects, this requirement for homology to the selector probe on both ends of the ligated probe increases specificity of the method by reducing detection of chimeras. In some cases, the first and second parts may comprise split portions of a barcode region and a mismatch in the portions of the barcode region may help increase specificity for the ligation and/or help identify mismatched portions of the barcode region (e.g., chimeric barcode region).

Nucleic acids and/or analytes that can be analyzed by the presently disclosed methods are described in greater detail in Section II.

II. Samples, Analytes, and Target Sequences

A. Samples

A sample disclosed herein can be or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a predisposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 µm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 µm. Thicker sections can also be used if desired or convenient, e.g., at least 70, 80, 90, or 100 µm or more. Typically, the thickness of a tissue section is between 1-100 µm, 1-50 µm, 1-30 µm, 1-25 µm, 1-20 µm, 1-15 µm, 1-10 µm, 2-8 µm, 3-7 µm, or 4-6 µm, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Postfixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprises one or more post-fixing (also referred to as postfixation) steps. In some embodiments, one or more post-fixing step is performed after contacting a sample with a polynucleotide disclosed herein, e.g., one or more probes such as a circular or padlock probe. In some embodiments, one or more post-fixing step is performed after a hybridization complex comprising a probe and a target is formed in a sample. In some embodiments, one or more post-fixing step is performed prior to a ligation reaction disclosed herein, such as the ligation to circularize a circularizable probe (e.g., a ligated probe that can be circularized using a selector probe as a template, as described herein).

In some embodiments, one or more post-fixing step is performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other suitable hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., *Science* 347(6221):543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DiR, DiD). Other cell membrane stains may include FM and RH dyes or immunohistochemical reagents specific for cell membrane proteins. In some examples, the stain may include but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Any suitable methods of destaining or discoloring a biological sample may be utilized, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay round. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete. In some embodiments, only a portion of crosslinked molecules in the reversibly cross-linked biological sample are de-crosslinked and allowed to migrate.

(viii) Tissue Permeabilization and Treatment

In some embodiments, a biological sample can be permeabilized to facilitate transfer of species (such as probes) into the sample. In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to opening up DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some aspects, the templated ligation probes and/or selector probes described herein can be used to perform an enrichment step. In some embodiments, one or more nucleic acid probes can be used to hybridize to a target nucleic acid (e.g., cDNA or RNA molecule, such as an mRNA) and ligated in a templated ligation reaction (e.g., RNA-templated ligation (RTL) or DNA-templated ligation (e.g., on cDNA)) to generate a product for analysis. In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample.

Figure 5A:
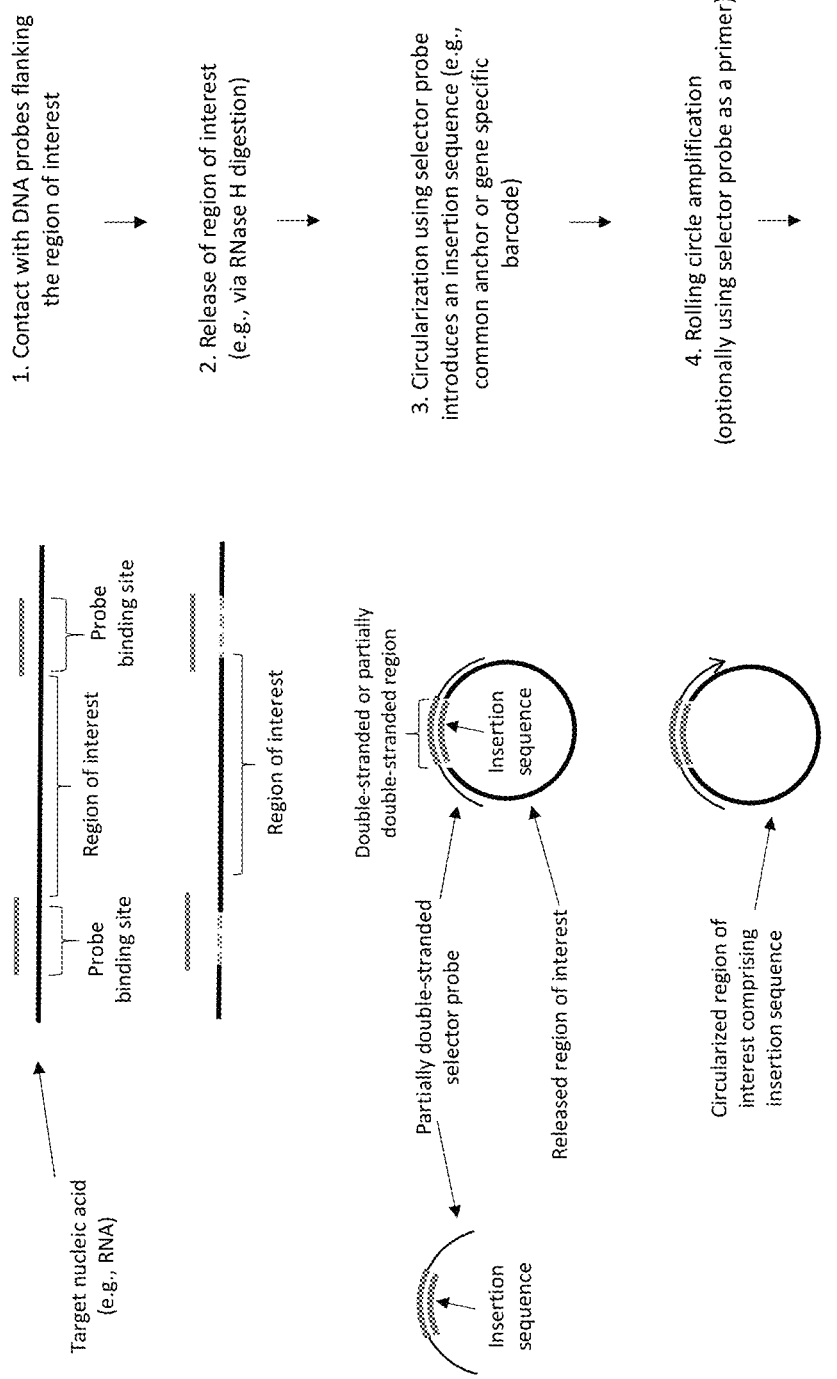
FIG. 5A-5B depict exemplary methods described herein. The method may comprise releasing a region of interest from a target nucleic acid in a biological sample. In some embodiments, the region of interest can be released from the target nucleic acid by hybridizing DNA probes (e.g., a first probe and a second probe) to cognate probe-binding sites flanking the region of interest in the target nucleic acid and then using RNase H digestion of target RNA hybridized to the DNA probes, as shown in FIG. 5A. In some embodiments, the region of interest can be released from the target nucleic acid (e.g., by restriction digest), as shown in FIG. 5B. The region of interest can then be circularized using a selector probe comprising a first strand and a second strand that form a partially double stranded probe, thereby generating a circularized region of interest comprising an insertion sequence from a double stranded or partially double-stranded region of the selector probe. The circularized fragment (e.g., comprising the region of interest) can then be amplified by rolling circle amplification. A sequence comprised by the circularized fragment and/or the insertion sequence can be detected in situ using sequencing by synthesis (SBS), sequencing by ligation (SBL), or sequencing by hybridization (SBH).
Figure 5B:
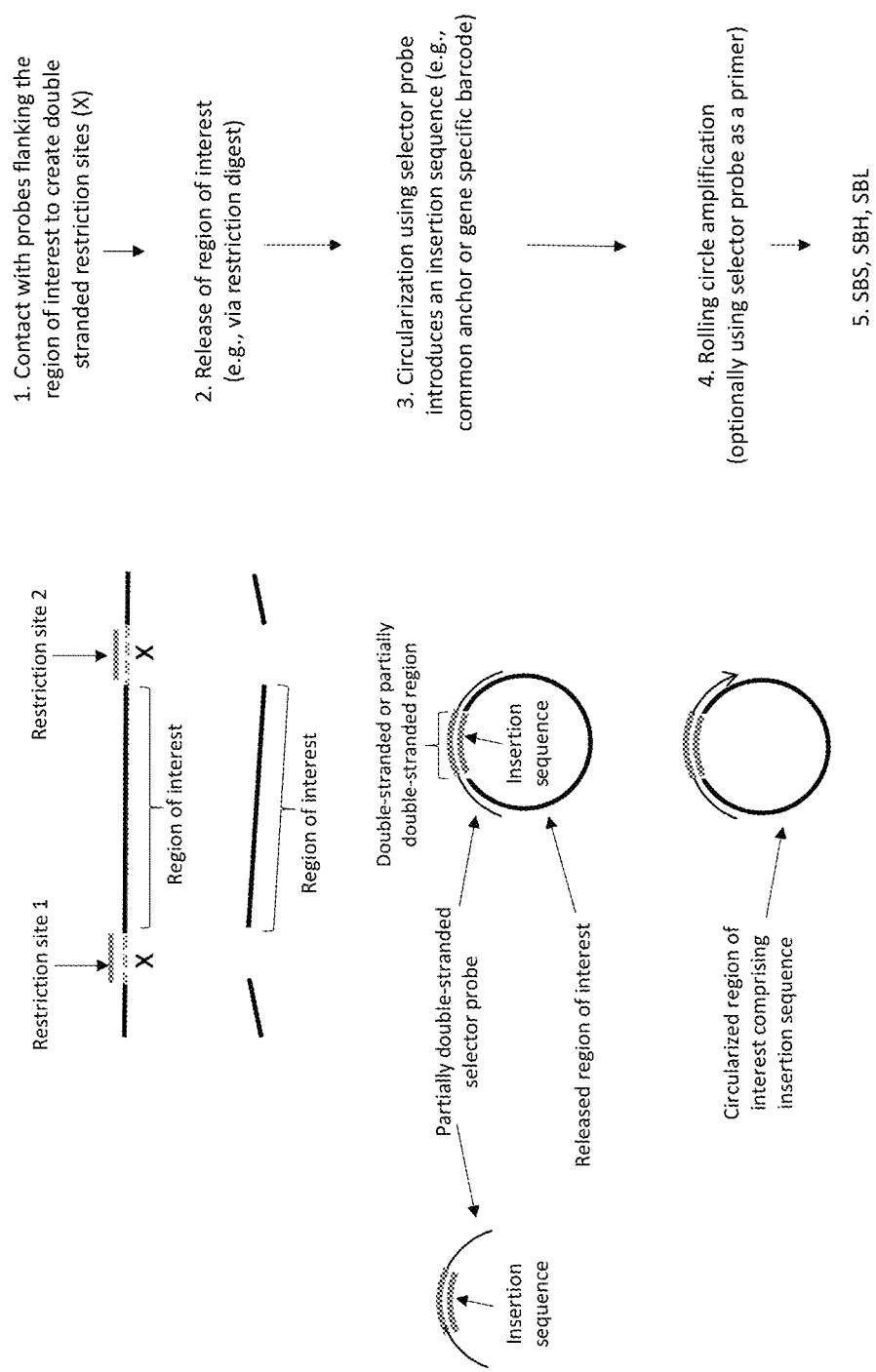

In some embodiments, a first and second probe can be used to hybridize to a target nucleic acid at cognate probe-binding sites at or adjacent to a region of interest in the target nucleic acid (e.g. RNA) as shown in FIG. 5A. For example, a region of interest from a target nucleic acid flanked by two cognate probe-binding sites in a biological sample can be released. In some embodiments, the region of interest can be released from the target nucleic acid by hybridizing probes (e.g., a first probe and a second probe) to cognate probe-binding sites flanking the fragment of interest in the target nucleic acid and then using RNase H digestion of target RNA hybridized to the DNA probes, as shown in FIG. 5A. In some embodiments, the region of interest can be released from the target nucleic acid (e.g., by restriction digest), as shown in FIG. 5B. In some embodiments, a first and second probe can be used to hybridize to a target nucleic acid at cognate probe-binding sites at or adjacent to a region of interest in the target nucleic acid (e.g. RNA) as shown in FIG. 5B to create double stranded sites for restriction enzyme digestion. For example, the first and second probes can be DNA probes. In some embodiments, the double stranded sites where the probe binds the target nucleic acid is a DNA-RNA hybrid. In some cases, restriction enzymes that cut single stranded nucleic acids can be used without using probes to first generate double stranded sites. In some embodiments, the region of interest is genomic DNA and the method comprises denaturaing or opening the target nucleic acid (e.g., using LNA or PNA). In some cases, the opened double stranded DNA allows the probes to bind the region of interest. In some embodiments, the target nucleic acid is a cDNA fragment generated using reverse transcription. The region of interest can then be circularized using a selector probe described herein. In some aspects, use of the selector probe(s) allows selective circularization of target nucleic acids of interest. In some embodiments, the region of interest comprises a mutation of interest.

An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using methods such as streptavidin beads.

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques*, 53(6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules (e.g., target nucleic acids), such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes (e.g., target nucleic acids) include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaR-NAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing or array technologies.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31(2):708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (e.g., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent (e.g., comprising a reporter oligonucleotide) that directly or indirectly binds to an analyte in the biological sample is analyzed.

In some embodiments, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labelling agent and each probe may comprise one or more barcode sequences. Exemplary templated ligation probes and selector probes for generating circular probes are described in Section III.

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agents. In some embodiments, the ligation product is an intramolecular ligation of an endogenous analyte. an intramolecular ligation product or an intermolecular ligation product, for example, the ligation product can be generated by the circularization of a circularizable probe or probe set upon hybridization to a target sequence or a selector probe. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof.

In some embodiments, a product is a primer extension product of an analyte, a labelling agent, a probe or probe set bound to the analyte (e.g., a circularizable probe bound to genomic DNA, mRNA, or cDNA), or a probe or probe set bound to the labelling agent (e.g., a circularizable probe bound to one or more reporter oligonucleotides from the same or different labelling agents).

C. Target Sequences

A target sequence for a probe disclosed herein (e.g., a templated ligation probe) may be comprised in any analyte disclose herein, including an endogenous analyte (e.g., a viral or cellular nucleic acid), a labelling agent, or a product or derivative of an endogenous analyte and/or a labelling agent. For example, a target sequence for a probe is comprised by a product generated by hybridizing a probe or probe set to an endogenous analyte and performing RCA using the probe or probe set.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In some embodiments, one or more barcodes of the probes (e.g., templated ligation probe or selector probe) are targeted by detectably labeled detection oligonucleotides, such as fluorescently labeled oligonucleotides. In some embodiments, various decoding schemes can be used to decode the signals, such as fluorescence, for sequence determination. In some embodiments, signals associated with an analyte can be detected as performed in sequential fluorescent in situ hybridization (seqFISH). In any of the preceding embodiments, barcodes (e.g., primary and/or secondary barcode sequences) can be analyzed (e.g., detected or sequenced) using any suitable methods or techniques, including those described herein, such as RNA sequential probing of targets (RNA SPOTs), sequential fluorescent in situ hybridization (seqFISH+), single-molecule fluorescent in situ hybridization (smFISH), or multiplexed error-robust fluorescence in situ hybridization (MERFISH). In some embodiments, the detection can comprise in situ sequencing. In some embodiments, the barcode detection steps can be performed as described in hybridization-based in situ sequencing (HybISS). In any of the preceding embodiments, barcodes can be analyzed (e.g., detected or sequenced) using any suitable methods or techniques, including those described herein, such as targeted in situ sequencing, fluorescent in situ sequencing (FISSEQ), sequencing by synthesis (SBS), sequencing by ligation (SBL), or sequencing by hybridization (SBH). In some embodiments, the barcode detection steps can be performed as described in spatially-resolved transcript amplicon readout mapping (STARmap). In any of the preceding embodiments, the methods provided herein can include analyzing the barcodes by sequential hybridization and detection with a plurality of labelled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5=1024$), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and U.S. Pat. Pub. 20210164039, which are hereby incorporated by reference in their entirety.

III. Templated Ligation Probes and Selector Probes for Generating Circular Probes Disclosed herein in some aspects are nucleic acid probes and/or probe sets (e.g., templated ligation probe comprising a first and second part, and selector probe) that are introduced into a cell or used to otherwise contact a biological sample such as a tissue sample. In some aspects, the nucleic acid probes and/or probe sets comprise a hybridization region comprising a target specific binding site (e.g., an interrogatory region), wherein the hybridization region on the probe is capable of hybridizing to a hybridization region on the target nucleic acid, wherein the hybridization region on the target nucleic acid comprises a region of interest.

The nucleic acid probes and/or probe sets may comprise any of a variety of entities that can hybridize to a nucleic acid, typically by Watson-Crick base pairing, such as DNA, RNA, LNA, PNA, etc. The nucleic acid probes typically contain a targeting sequence that is able to directly or indirectly bind to at least a portion of a target nucleic acid. The nucleic acid probes may be able to bind to a specific target nucleic acid (e.g., an mRNA, or other nucleic acids as discussed herein). In some embodiments, the nucleic acid probes may be detected using a detectable label, and/or by using secondary nucleic acid probes able to bind to the nucleic acid probes. In some embodiments, the nucleic acid probes (e.g., primary probes and/or secondary probes) are compatible with one or more biological and/or chemical reactions. For instance, a nucleic acid probe disclosed herein can serve as a template or primer for a polymerase, a template or substrate for a ligase, a substrate for a click chemistry reaction, and/or a substrate for a nuclease (e.g., endonuclease or exonuclease for cleavage or digestion).

Provided herein are methods involving the use of one or more probes for analyzing one or more target nucleic acid(s), such as a target nucleic acid (for example, a messenger RNA) present in a cell or a biological sample, such as a tissue sample. Also provided are probes, sets of probes, compositions, kits, systems, and devices for use in accordance with the provided methods. In some aspects, the provided methods and systems can be applied to detect, image, quantitate, or determine the presence or absence of one or more target nucleic acid(s) or portions thereof (e.g., presence or absence of sequence variants such as point mutations and SNPs). In some aspects, the provided methods can be applied to detect, image, quantitate, or determine the sequence of one or more target nucleic acid(s), comprising sequence variants such as point mutations and SNPs.

In some aspects, the provided embodiments can be employed for in situ detection and/or sequencing of a target nucleic acid in a cell, e.g., in cells of a biological sample or a sample derived from a biological sample, such as a tissue section on a solid support, such as on a transparent slide.

In some aspects, the provided methods involve a step of contacting, or hybridizing, one or more polynucleotides, such as any of the probes described herein, to a cell or a sample containing a target nucleic acid with a region of interest in order to form a hybridization complex. In some aspects, the provided methods comprise one or more steps of ligating the polynucleotides, for instance of ligating the probes to form a circular probe. In some aspects, the provided methods involve a step of amplifying one of the polynucleotides (e.g., a circular probe), to generate an amplification product. In some aspects, the provided methods involve a step of detecting and/or determining the sequence of all or a portion of the amplification product (for example, of one or more barcodes contained in the amplification product) and/or one or more of the polynucleotides, for instance the circular probe, with or without amplification, for instance any barcodes contained therein. In some aspects, the provided methods involve performing one or more of the steps described herein, simultaneously and/or sequentially.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, a method for spatially profiling analytes such as the transcriptome or a subset thereof in a biological sample is provided. Methods, compositions, kits, devices, and systems for these in situ assays, comprising spatial genomics and transcriptomics assays, are provided. In some embodiments, a provided method is quantitative and preserves the spatial information within a tissue sample without physically isolating cells or using homogenates. In some embodiments, the present disclosure provides methods for high-throughput profiling one or more single nucleotides of interest in a large number of targets in situ, such as transcripts and/or DNA loci, for detecting and/or quantifying nucleic acids in cells, tissues, organs or organisms.

In some embodiments, a circularizable probe (e.g., a ligated probe that can be circularized using a selector probe as a template) disclosed herein includes one or more barcode sequences. In some embodiments, one or more barcode sequences are in the insertion sequence of the selector probe. The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some aspects, the provided methods are employed for in situ analysis of target nucleic acids, for example for in situ sequencing or multiplexed analysis in intact tissues or a sample with preserved cellular or tissue structure. In some aspects, the provided methods can be used to detect or determine the identity or amount in situ of single nucleotides of interest in target nucleic acids, for instance of single nucleotide polymorphisms of genes of interest. In some embodiments, the first molecule can comprise an interrogatory region complementary to a region of interest comprised by the target nucleic acid. In some embodiments, the interrogatory region comprised by the templated ligation probe is one or more, or 2, 3, 4, 5, or more nucleotides in length.

Figure 2:
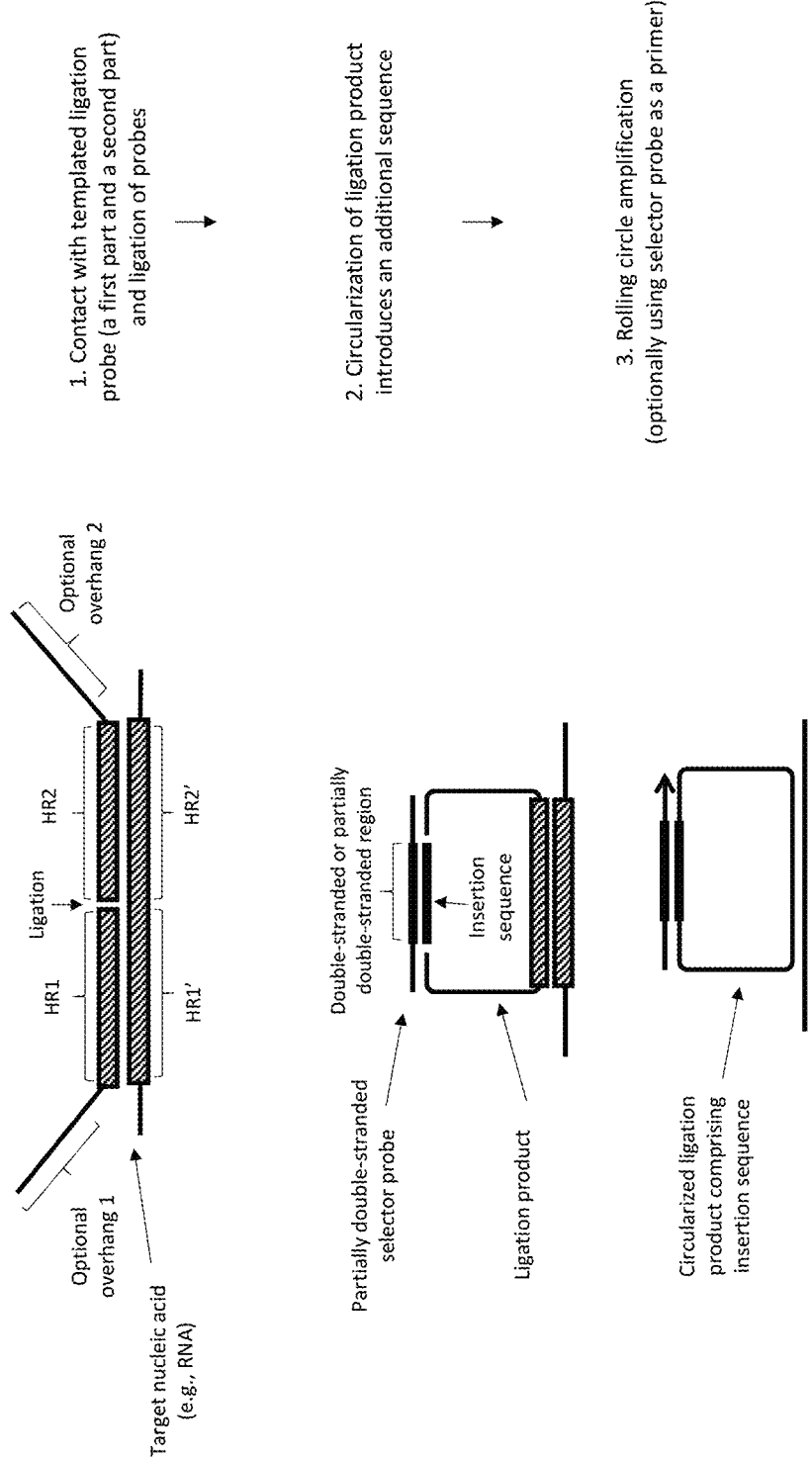
FIG. 2 depicts an exemplary method described herein, wherein the first part and the second part of the templated ligation probes comprise overhang regions that do not hybridize to the target nucleic acid. Thus, the ligated probe does not need to be released from the target nucleic acid to allow hybridization of the selector probe. In some embodiments, the overhang regions can correspond to the target sequence. In some embodiments, using overhang sequences corresponding to the target sequence further increases the specificity of the method by preventing or reducing formation of chimeric circularized ligated probes.

In some aspects, as shown in FIGS. 1-2, provided herein is a method for analyzing a biological sample, comprising contacting the biological sample comprising a target nucleic acid (e.g., RNA or DNA) with a templated ligation probe (e.g., an RNA-templated ligation probe or a DNA-templated ligation probe) comprising a first part and a second part, wherein at least one of the first part and the second part comprises a target specific binding site which is complementary to a cognate probe-binding site at or adjacent to a region of interest in the target nucleic acid. The first part and the second part hybridize to the target nucleic acid such that ligatable ends of the first and second parts are juxtaposed for ligation to each other using the target nucleic acid as a ligation template. The first and second parts are ligated using the target nucleic acid as a template, thereby generating a ligated probe. In some embodiments, the first part and/or second part comprises one or more ribonucleotides at and/or near a ligatable 3' end of the first part and/or second part. In some embodiments, the first part and/or second part comprises a ribonucleotide at its 3' end.

The ligation can comprise using a ligase selected from the group consisting of a *Chlorella* virus DNA ligase (PBCV DNA ligase), a T4 RNA ligase, a T4 DNA ligase, and a single-stranded DNA (ssDNA) ligase. In particular embodiments, a PBCV-1 DNA ligase or variant or derivative thereof and/or a T4 RNA ligase 2 (T4 Rnl2) or variant or derivative thereof can be used. For instance, Rnl2 (dsRNA Ligase) is an ATP-dependent dsRNA ligase that efficiency seals 3'-OH/5'-PO$_4$ nicks in duplex RNAs. This process can occur via adenylation of the ligase, AMP transfer to the 5'-PO$_4$ on the donor strand, and the attack by the acceptor strand 3'-OH on the 5'-adenylylated donor strand, resulting in the formation of the covalent phosphodiester linkage. In some embodiments, the ligase such as Rnl2 can tolerate complete substitution of its duplex RNA substrate with deoxyribonucleotides, e.g., when the 3'-terminus of the acceptor strands terminates in one or more ribonucleotides, such as a ribonucleotides or a diribonucleotide. In some embodiment, the donor probe providing the 5'-PO$_4$ terminus can comprise only deoxyribonucleotides, which undergo highly efficient, template-dependent ligation to an RNA-DNA hybrid acceptor probe which comprises deoxyribonucleotides and 3'-ribonucleotide or 3'-diribonucleotides.

In some embodiments, two or more parts may be ligated using the target nucleic acid as a template to form a ligated multi-partite probe. In some embodiments, the ligated multi-partite probe can be released from the target nucleic acid (e.g., RNA). In some embodiments, the ligated probe may be released from the target nucleic acid by an endonuclease, such as RNase H (e.g., RNase H1 or RNase H2), RNase A, RNase If, RNase HII, and/or RNase HIII. Once probes are ligated, the ligated multi-partite probe may be released from the target nucleic acid (e.g., RNA template) so that it may be recovered, e.g., via ligation to a selector probe disclosed herein, and then analyzed (e.g., via RCA). RNase H may be used to release the ligated multi-partite probe, e.g., as shown in FIG. 1. RNase H belongs to a family of non-sequence-specific endonucleases that catalyze the cleavage of RNA via a hydrolytic mechanism. RNase H can specifically degrade only the RNA in RNA:DNA hybrids and can be used to destroy the RNA template after first-strand cDNA synthesis by reverse transcription, as well as in procedures such as nuclease protection assays. RNase H can also be used to degrade specific RNA strands when the cDNA oligonucleotide is hybridized, such as the removal of the polyadenine tail from mRNA hybridized to oligo (dT), or the destruction of a chosen non-coding RNA inside or outside the living cell. RNase H specifically hydrolyzes the phosphodiester bonds of RNA, which is hybridized to DNA. This enzyme does not digest single or double-stranded DNA. To terminate the reaction, a chelator, such as EDTA, is often added to sequester the metal ions in the reaction mixture, or the enzyme can be heat destroyed.

In some embodiments, the ligated multi-partite probe can remain hybridized to the target nucleic acid (e.g., DNA or RNA). In some embodiments, the ligated multi-partite probe can comprise one or more free ends, e.g., as shown in FIG. 2. In some embodiments, the free ends (overhang 1 and overhang 2) can comprise adapter regions corresponding to the target sequence and/or region of interest, or can comprise common adapter regions. The adapter regions of the overhang(s) can hybridize to the selector probe. In some embodiments, the overhang(s) can further comprise one or more additional sequences (e.g., anchor sequences, primer binding sequences, and/or barcode sequences or comeplements thereof). In some embodiments, the ligated multi-partite probe can comprise a split barcode region as shown in FIG. 3A and FIG. 3B, wherein the first part of the templated ligation probe comprises an overhang comprising a first portion of the barcode region and the second part of the templated ligation probe comprises an overhang comprising a second portion of the barcode region. The first portion and the second portion of the barcode region that are not connected by a phosphodiester linkage can be considered a "split" barcode region. After ligation of the first part and the second part to form the ligated multi-partite probe, the first end and second end of the ligated multipartite probe comprise overhang regions comprising a first portion and second portion of the barcode region, respectively.

FIGS. 3A-3C show an exemplary set of probes and method described herein, wherein the ligated probe formed from the first and second part of the templated ligation probe comprises a split barcode region. FIG. 3A depicts an exemplary set of probes wherein the overhang region of the first part and the overhang region of the second part of the templated ligation probes comprise a first and second portion of a barcode region, respectively, and the selector probe hybridizes to the first and second portion of the barcode region. The selector probe comprises a first strand and a second strand that form a partially double-stranded probe, wherein the first strand comprises a first homology arm complementary to the first portion of the barcode region, a second homology arm complementary to the second portion of the barcode region, and a region that hybridizes to the second strand. The second strand comprises an insertion sequence.

In some embodiments, the insertion sequence can be an additional barcode region or an additional portion of the barcode region. Thus, ligation of the insertion sequence to both ends of the ligated probe can form the complete barcode region. In some embodiments, formation of the complete barcode region can allow for detection of the complete barcode region or a complement thereof (e.g., by fluorescent in situ hybridization and/or by sequencing by hybridization). For example, detection probes can be designed that stably hybridize to the complete barcode region or a complement thereof (comprising the first portion, second portion, and additional (middle) portion. Thus, in some embodiments, following circularization of the ligated probe using the selector probe, the first portion of the barcode region, the insertion sequence (an additional portion of the barcode region), and the second portion of the barcode region together form a complete barcode region. In some embodiments, the method comprises performing rolling circle amplification of the circularized probe to generate an RCA product comprising multiple copies of the complement of (i) the first portion of the barcode, (ii) the insertion sequence (e.g., an additional portion of the barcode region), and (iii) the second portion of the barcode. In some embodiments, the RCA product comprises multiple copies of the complete barcode region. In some embodiments, the complement of the complete barcode region is detected according to any of the detection methods described in Section V below (e.g., sequencing by hybridization and/or sequencing by ligation).

In some embodiments, the insertion sequence can have one or more functions, e.g., as an anchor sequence for detection and/or as a sequence for binding a sequencing primer (e.g., for performing sequencing by ligation (SBL)). In some embodiments, the insertion sequence can comprise an anchor sequence. In some embodiments, an "anchor sequence" is a known sequence for hybridization of an anchor probe (e.g., a detection anchor probe), wherein the anchor probe can hybridize to the anchor sequence or a complement thereof. In some aspects, ligation of the insertion sequence to the ends of the ligated probe (e.g., first and second parts) can introduce a common anchor sequence to a plurality of ligated probes, thereby allowing detection of various target nucleic acids at the same time. An anchor sequence can be common among a plurality of circularized ligated probes to allow hybridization of an anchor probe to a plurality of circularized ligated probes or rolling circle amplification products thereof. In some embodiments, a plurality of insertion sequences can be used, wherein a first subset of all target nucleic acids can be associated with a first common anchor sequence, a second subset of all target nucleic acids can be assocatied with a second common anchor sequence, etc. By using a plurality of common anchor sequences, a subset of target nucleic acids, wherein each subset is associated with various target nucleic acids, can be detected at the same time. A primer binding sequence is a sequence for hybridization of a primer (e.g., a sequencing primer for SBL), wherein the primer hybridizes to the primer binding sequence or a complement thereof. In some cases, an insertion sequence can be used for detection by binding detectably labeled anchor probes as described and the same sequence can be used as a primer binding sequence for SBL. In some embodiments, an insertion sequence can comprise a primer binding sequence and an anchor sequence, wherein the primer binding sequence and anchor sequence are different sequences.

In some embodiments, the method comprises performing rolling circle amplification of the circularized probe to generate an RCA product comprising multiple copies of the complement of (i) the first portion of the barcode, (ii) the insertion sequence, and (iii) the second portion of the barcode. In some examples, the insertion sequence comprises a sequencing primer binding sequence or complement thereof. In some embodiments, the method comprises contacting the biological sample with a sequencing primer that hybridizes to the sequencing primer binding sequence or complement thereof in the RCA product, and performing sequencing by ligation (SBL) using the sequencing primer. In some embodiments, the SBL comprises ligating one or more detection probes to the sequencing primer, wherein the one or more detection probes are complementary to a region adjacent to the sequencing primer binding sequence or complement thereof in the RCA product, thereby determining a sequence of one or more bases of the region adjacent to the sequencing primer binding sequence. In some embodiments, the method comprises contacting the biological sample with a first sequencing primer that hybridizes to a first portion of the sequencing primer binding sequence and ligating one or more detection probes to the first sequencing primer, thereby determining a sequence of one or more bases of a region adjacent to the first portion of the sequencing primer binding sequence, and contacting the biological sample with a second sequencing primer that hybridizes to a second portion of the sequencing primer binding sequence and ligating one or more detection probes to the second sequencing primer, thereby determining a sequence of one or more bases of a region adjacent to the second portion of the sequencing primer binding sequence. In some embodiments, the first portion and second portion of the sequencing primer binding sequence are overlapping sequences of different lengths (e.g., lengths that differ by 1, 2, 3, 4, or more nucleotides). In some aspects, the sequencing primer binding sequence is the complement of the insertion sequence. In some embodiments, the first portion and second portion of the complement of the insertion sequence are overlapping regions that are offset by one or more nucleotides (e.g., are offset by 1, 2, 3, 4, or more nucleotides). In some embodiments, the complement of the insertion sequence comprises sequences complementary to a set of sequencing primers (e.g., a set of 2, 3, 4, or more sequencing primers) that hybridize to the complement of the insertion sequence at positions offset by 1, 2, 3, 4, or more nucleotides.

In some embodiments, the method comprises contacting the biological sample with a detectably labeled anchor probe, wherein the detectably labeled anchor probe hybridizes to the complement of the anchor sequence in a plurality of RCA products, thereby detecting the plurality of RCA products (e.g., associated with various different target nucleic acids) in the sample. In some embodiments, the plurality of RCA products is a subset of the RCA products in the sample, and the method comprises contacting the sample with a second detectably labeled anchor probe, wherein the second detectably labeled anchor probe hybridizes to the complement of a second anchor sequence in the second subset of RCA products in the sample. The detectably labeled anchor probe can be directly or indirectly labeled with a detectable moiety, such as any of the detectable moieties described in Section V below.

The method can comprise contacting the biological sample with a selector probe comprising a first strand and a second strand that form a partially double stranded probe as shown in FIGS. 1-2, wherein the first strand comprises a first homology arm complementary to a first end of the ligated probe, a second homology arm complementary to a second end of the ligated probe, and a region that hybridizes to the second strand, and wherein the second strand comprises an insertion sequence. In some aspects, common adapter regions on the ligated probe may allow for the use of a common selector probe for the circularization step to generate the circularized ligated probe. In some cases, the common selector probe can be used to circularize a plurality of ligated first and second part of the templated ligation probe comprising various hybridization regions for detecting a plurality of target nucleic acids. The ligated probe is circularized using the selector probe as a template, thereby generating a circularized ligated probe comprising the insertion sequence from a double stranded or partially double-stranded region of the selector probe. The circularized probe can be amplified by rolling circle amplification of the circularized ligated probe in the biological sample to generate a rolling circle amplification product. One or more sequences of circularized probes and/or rolling circle amplification products thereof can be detected as described in Section V below.

In some embodiments, the insertion sequence is a common sequence (e.g., an anchor sequence or a sequencing primer binding sequence that is common among a plurality of circularized ligated probes). In some embodiments, an anchor sequence or complement thereof hybridizes to an anchor probe or sequencing primer binding sequence for one target nucleic acid can also hybridize to another nucleic acid molecule in the sample (e.g., the target nucleic acid). In some cases, a common sequence can be provided for immobilizing the ligated probe in the sample. In some embodiments, an anchor sequence or complement thereof hybridizes to a detection anchor probe (e.g., for simultaneously detecting a plurality of RCA products in the sample associated with different target nucleic acids). In some embodiments, a sequencing primer binding sequence or complement thereof hybridizes to a sequencing primer for a sequencing-by-ligation (SBL) based chemistry. In SBL, short fluorescently labeled oligonucleotides complementary to a portion of a nucleic acid (e.g., hybridized to the circularized templated ligation probe, optionally to a barcode sequence comprised by the circularized templated ligation probe) are ligated to adjacent sequencing primers hybridized to the nucleic acid. In some embodiments, a common sequence can be hybridized to an anchor probe (e.g., hybridized to the anchor sequence comprised by the circularized templated ligation probe, optionally wherein the anchor sequence is comprised by the insertion sequence).

In some embodiments, the method comprises contacting the sample with a sequencing primer that hybridizes to sequencing primer binding sequence comprised by the circularized templated ligation probe or an amplification product thereof (e.g., a sequence comprised by the insertion sequence and added to the circularized templated ligation probe using the selector probe, or a complement thereof). In some embodiments, the method comprises performing sequencing by ligation (SBL) from a 5' end of the sequencing primer and/or performing SBL from a 3' end of the sequencing primer, thereby sequencing one or more regions of the circularized templated ligation probe or an amplification product thereof. In some embodiments, the one or more regions sequenced by SBL include one or more barcode regions (e.g., comprised by overhang regions of the first part and/or second part of the templated ligation probe). In some embodiments, the one or more regions sequenced by SBL include portions of the templated ligation probe that hybridize to the target nucleic acid in the sample, thereby identifying the target nucleic acid.

In some embodiments, the homology arms of the selector probes comprising common sequences (e.g., anchor sequences) hybridize to common sequences in the templated ligation probes (e.g., the selector probe is cognate to a plurality of templated ligation probes). For example, the homology arms of selector probes comprising common insertion sequences can hybridize to common adapter regions comprised by overhangs of the first and second part of the templated ligation probe. In other embodiments, homology arms of selector probes comprising common insertion sequences (e.g., anchor sequences) hybridize to unique adapter regions comprised by overhangs of the first and second part of the templated ligation probe. Thus, a selector probe may be cognate to a particular ligation probe out of a plurality of ligation probes despite comprising a common insertion sequence.

Figure 4A:
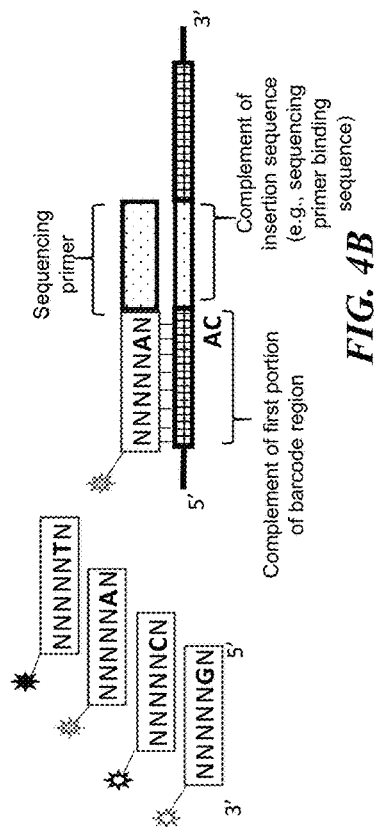
FIGS. 4A-4C show an exemplary method of sequencing the complement of a barcode sequence or a portion of the barcode sequence or complement thereof comprised by RCA product of the circularized ligated probe using sequencing by ligation (SBL), wherein a sequencing primer hybridizes to the complement of the insertion sequence (e.g., serving as a sequencing primer binding site for SBL). In some embodiments, the method comprises sequencing a first and/or second portion of the barcode sequence or complement thereof comprised by the RCA product.
Figure 4B:
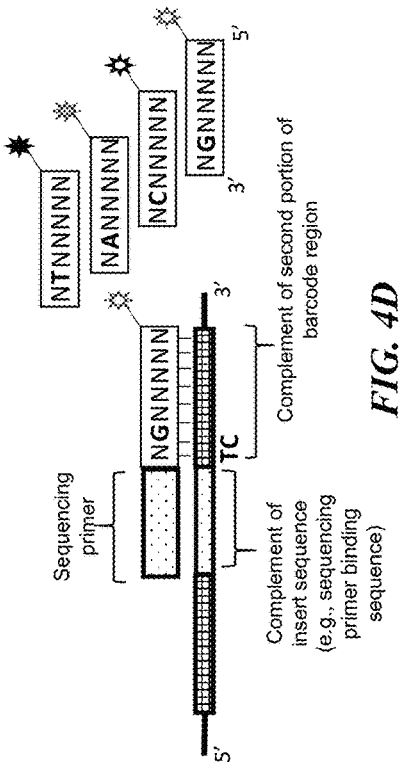
Figure 4C:
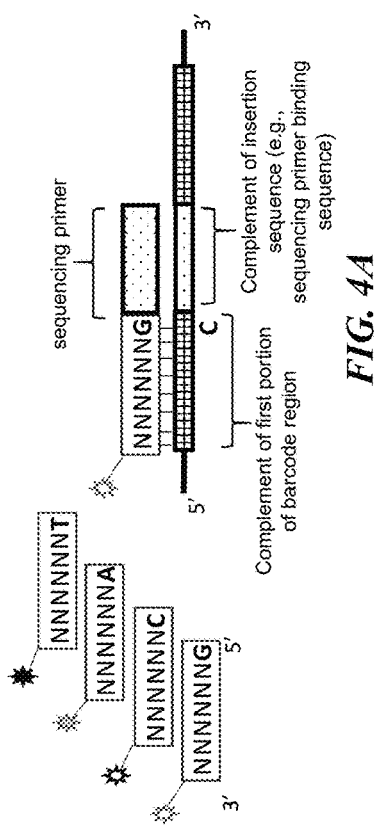
Figure 4D:
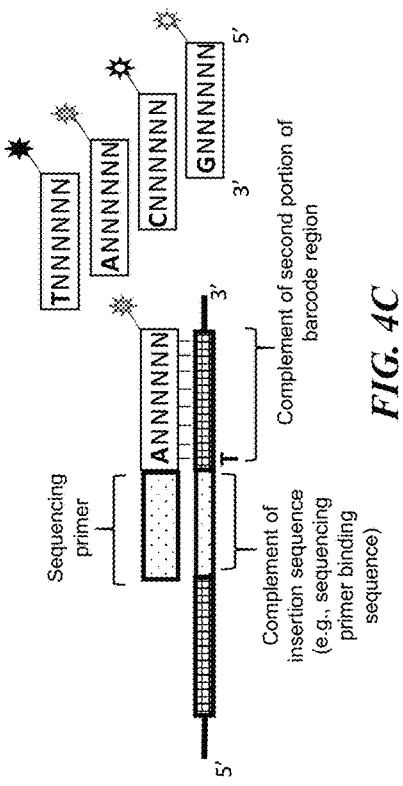

In some embodiments, the homology arms of the selector probe hybridize to a first portion and second portion of a barcode region in the ligated probe, as shown in FIG. 3A. In some embodiments, the insertion sequence is a common sequence, such as an sequencing primer binding sequence. In some embodiments, the method comprises contacting the sample with a sequencing primer that hybridizes to the sequencing primer binding sequence comprised by the circularized ligated probe or a complement of the insertion sequence comprised by an amplification product of the circularized ligated probe, and performing SBL to determine the sequence of the first and/or second portions of the barcode sequence. In some embodiments, the first and second portions of the barcode sequence are separated by the insertion sequence (e.g., sequencing primer binding sequence). In some embodiments, the method comprises performing SBL from a 3' end of the sequencing primer to determine the sequence of a portion of the barcode region or complement thereof that is 5' of the sequencing primer binding sequence or complement thereof, as shown in FIGS. 4A-4B. In some embodiments, the method comprises performing SBL from a 5' end of the sequencing primer to determine the sequence of a portion of the barcode region or complement thereof that is 3' of the sequencing primer binding sequence or complement thereof, as shown in FIGS. 4C-4D. In some embodiments, the method comprises performing SBL in both the 5' and 3' direction to determine the sequence of a first portion of the barcode region or complement thereof and the sequence of a second portion of the barcode region or complement thereof, wherein the first portion of the barcode region and the second portion of the barcode region are flanking the sequencing primer binding sequence. Methods of detecting a sequence by SBL are described in more detail in Section V below. In some embodiments, the homology arms of the selector probe comprise sequences corresponding the target nucleic acid or a region of interest thereof, and the insertion sequence comprises a sequence corresponding to the target nucleic acid or region of interest thereof (e.g., a barcode sequence). In some embodiments, the homology arms comprising sequences corresponding to the target nucleic acid or region of interest thereof hybridize to ends of the ligated probe that were hybridized to the target nucleic acid (e.g., after releasing the ligated probe from the target nucleic acid). In some embodiments, the homology arms comprising sequences corresponding to the target nucleic acid or region of interest thereof hybridize to adapter regions corresponding to the target nucleic acid or region of interest thereof, wherein the adapter regions are comprised by overhangs of the first and second part.

In some embodiments, the first part and/or second part of the templated ligation probe comprises an interrogatory region complementary to a region of interest in the target nucleic acid. In some embodiments, the templated ligation of the first and second part depends on hybridization of the interrogatory region to the region of interest. In some embodiments, the interrogatory region comprises a terminal nucleotide of the first part or second part of the templated ligation probe that is hybridized to the target nucleic acid and juxtaposed with the other part of the probe for ligation. In some embodiments, the interrogatory region comprises a 3' terminal nucleotide of the first part or second part of the templated ligation ligation probe that is hybridized to the target nucleic acid and juxtaposed with the other part of the probe for ligation. In some embodiments, the first part and/or second part comprises one or more ribonucleotides, optionally wherein the second molecule and/or third molecule comprises no more than four consecutive ribonucleotides. In some embodiments, the one or more ribonucleotides are at and/or near a ligatable 3' end of the first part and/or second part. In some embodiments, the first part and/or second part comprises a ribonucleotide at its 3' end.

In some embodiments, the first part hybridizes to an upstream (e.g., 5') region of the target nucleic acid, and the second part hybridizes to a downstream (e.g., 3') region of the target nucleic acid. In some embodiments, the 5' end of the first part is juxtaposed with the 3' end of the second part for ligation of the first and second parts. In some embodiments, the first part comprises a 3' overhang and/or the second part comprises a 5' overhang. In some embodiments, the interrogatory region comprises the 3' end of the second part.

In some embodiments, the second part hybridizes to an upstream (e.g., 5') region of the target nucleic acid, and the first part hybridizes to a downstream (e.g., 3') region of the target nucleic acid. In some embodiments, the 5' end of the second part is juxtaposed with the 3' end of the first part for ligation of the first and second parts. In some embodiments, the second part comprises a 3' overhang and/or the first part comprises a 5' overhang. In some embodiments, the interrogatory region comprises the 3' end of the first part.

The first part and/or second part can comprise DNA residue(s) and/or RNA residue(s). In some embodiments, the first part and/or second part can comprise primarily DNA and one or more ribonucleotides e.g., no more than four consecutive ribonucleotides. In some embodiments, the one or more ribonucleotides are at and/or near a ligatable 3' end of the first part and/or second part of the templated ligation probe.

In some embodiments, the first part and second part are each independently between 5 nucleotides and 60 nucleotides in length, or more than 60 nucleotides in length. In some embodiments, the first part and second part are each independently between 5 and 10, between 10 and 15, between 15 and 20, between 20 and 25, between 25 and 30, between 30 and 35, between 35 and 40, between 40 and 45, between 45 and 50, between 50 and 55, between 55 and 60, or more than 60 nucleotides in length.

In some embodiments, the first part of the templated ligation probe hybridizes to the target nucleic acid via its target-specific binding site (e.g., hybridization region 1 or HR1 as shown in FIGS. 1-2). In some embodiments, the target specific binding site of the first part of the templated ligation probe is between 5 and 10, between 10 and 15, between 15 and 20, between 20 and 25, between 25 and 30, between 30 and 35, between 35 and 40, between 40 and 45, between 45 and 50, between 50 and 55, between 55 and 60, or more than 60 nucleotides in length.

In some embodiments, the second part of the templated ligation probe hybridizes to the target nucleic acid via its target-specific binding site (e.g., hybridization region 2 or HR2 as shown in FIGS. 1-2). In some embodiments, the target specific binding site of the second part of the templated ligation probe is between 5 and 10, between 10 and 15, between 15 and 20, between 20 and 25, between 25 and 30, between 30 and 35, between 35 and 40, between 40 and 45, between 45 and 50, between 50 and 55, between 55 and 60, or more than 60 nucleotides in length.

In some embodiments, the first part and/or second part comprise overhang region(s), as shown in FIG. 2. In some embodiments, the first part comprises a first overhang (overhang 1), and the second part comprises a second overhang (overhang 2). In some embodiments, overhang 1 and overhang 2 are each independently between 5 nucleotides and 60 nucleotides in length, or more than 60 nucleotides in length. In some embodiments, the overhang 1 and overhang 2 are each independently between 5 and 10, between 10 and 15, between 15 and 20, between 20 and 25, between 25 and 30, between 30 and 35, between 35 and 40, between 40 and 45, between 45 and 50, between 50 and 55, between 55 and 60, or more than 60 nucleotides in length.

In some embodiments, provided herein is a set comprising a plurality templated ligation probes for detecting a plurality of distinct target sequences. In some embodiments, a probe of the plurality (e.g., after ligation using the target nucleic acid as a template) comprises a first end and/or second end that corresponds to the target sequence (e.g., the ends of the ligated probe can uniquely correspond to a target sequence of the plurality of target sequences. In some embodiments, a target-specific selector probe is used to circularize the ligated probe(s). In some embodiments, the insertion sequence is target specific (e.g., a barcode sequence). In some embodiments, the first end and/or second end of a ligated probe of the plurality of probes comprise sequences that are common to the first end and/or second end of at least one other ligated probe of the plurality of probes. In some embodiments, the first end and/or second end comprise sequences that are common among all ligated probes of the plurality of probes, or among a subset of ligated probes among the plurality of probes. For example, templated ligation probes of the plurality can be designed to target the same gene and to recognize different sequences of a region of interest in the gene. In some embodiments, the common sequences at the end of the ligated probes could be common among probes recognizing that gene, but distinct from probes recognizing another gene. In some embodiments, each of the probes can comprise a target-specific barcode, and a common selector probe (e.g., a selector probe common to the subset of probes recognizing a given gene) can be used to insert a common insertion sequence (e.g., an anchor or primer sequence) to all of a subset of the circularized probes.

In some embodiments, the method comprises contacting the sample with a plurality of templated ligation probes corresponding to a plurality of target sequences. In some embodiments, the method comprises contacting the sample with a common selector probe (e.g., comprising common homology arms and a common insertion sequence such as an anchor or primer sequence). In some embodiments, the method comprises contacting the sample with a plurality of selector probes corresponding to the plurality of target nucleic acids. In some cases, a selector probe corresponds to a target nucleic acid. In some embodiments, a selector probe of the plurality comprises an insertion sequence comprising a barcode corresponding to the target nucleic acid.

In some embodiments, the first homology arm of the selector probe is one or more or 2, 3, 4, 5, 6, 7, 8, 9, or 10 or more nucleotides in length. In some embodiments, the first homology arm of the selector probe is between 5 and 10, between 10 and 15, between 15 and 20, between 20 and 25, between 25 and 30, or more than 30 nucleotides in length. In some embodiments, the second homology arm of the selector probe is one or more or 2, 3, 4, 5, 6, 7, 8, 9, or 10 or more nucleotides in length. In some embodiments, the second homology arm of the selector probe is between 5 and 1, between 10 and 15, between 15 and 20, between 20 and 25, between 25 and 30, or more than 30 nucleotides in length. The first and second homology arms of the selector probe can be the same length or different lengths.

In some embodiments, the insertion sequence is one or more or 2, 3, 4, 5, 6, 7, 8, 9, or 10 or more nucleotides in length. In some embodiments, the first homology arm of the selector probe is between 5 and 10, between 10 and 15, between 15 and 20, between 20 and 25, between 25 and 30, between 30 and 35, between 35 and 40, between 40 and 45, between 45 and 50, between 50 and 60, between 60 and 100, or more than 100 nucleotides in length. In some embodiments, the insertion sequence comprises one or more common sequences (e.g., for hybridization of anchor probes and/or primers). In some embodiments, the insertion sequence comprises one or more target specific sequences (e.g., barcode sequences).

In some embodiments, the selector probe functions to circularize RNA. In some embodiments, the first and second strand of the selector probe comprise RNA. In some embodiments, the selector probe is an RNA-DNA hybrid. In some embodiments, the first strand of the selector probe comprises DNA and the second strand of the selector probe comprises RNA. In some embodiments, the insertion sequence is an RNA sequence. In other embodiments, the selector probe can comprise only DNA and the insertion sequence can be a DNA sequence.

In some embodiments, a selector probe disclosed herein does not comprise a common sequence. For example, the selector probe can comprise target-specific homology arms for insertion of a target-specific common sequence such as a barcode.

In some embodiments, target-specific homology arms of a selector probe will not hybridize to both ends of a chimeric ligated probe (e.g., a probe generated due to non-specific hybridization and ligation of a first part targeting sequence A and a second part targeting sequence B). The chimeric ligated probe can comprise, for example, a first end corresponding to A and a second end corresponding to B. Optionally, the first end is a first overhang A and the second end is a second overhang B. In some embodiments, a selector probe A will only circularize probes comprising a first end A (adapter region A) and a second end A (adapter region A), and a selector probe B will only circularize probes comprising a first end B (adapter region B) and a second end B (adapter region B). Chimeric probes comprising a first part A ligated to a second part B or vice versa will not hybridize to both homology arms of the selector probe, and thus are not circularized by the selector probe. In some embodiments, mismatched but ligated first part and second part of the template ligation probe (e.g., chimeric ligated probe) may indicate non-specific hybridization has occurred and the mismatch can be detected. In some examples, a mismatched can be detected if barcodes are included on the overhangs of the ligated template ligation probe.

In some embodiments, the selector probe (or another primer or anchor molecule) is immobilized in the biological sample and/or a matrix embedding the biological sample. In some embodiments, the selector probe, primer, or anchor can be immobilized in the sample prior to generating an amplification or extension product as described in Section IV. In some embodiments, the first strand of the selector probe is immobilized in the biological sample and/or a matrix embedding the biological sample. In some embodiments, the first strand of the selector probe is immobilized at its 5' end and is used as a primer to generate the rolling circle amplification product of the circularized ligated probe. For example, in some embodiments, the first strand of the selector probe comprises a 5' acrydite moiety for immobilization in the sample and/or matrix.

IV. Ligation, Extension, and Amplification

In some aspects, after formation of a hybridization complex comprising nucleic acid probes and/or probe sets described in Section III and the target nucleic acids, the assay further comprises one or more steps such as ligation, extension and/or amplification of the probe or probe set hybridized to the target nucleic acid. In some embodiments, the methods of the invention include the step of performing rolling circle amplification in the presence of a target nucleic acid of interest.

In some embodiments, the ligation involves chemical ligation (e.g., click chemistry ligation). In some embodiments, the chemical ligation involves template dependent ligation. In some embodiments, the chemical ligation involves template independent ligation. In some embodiments, the click reaction is a template-independent reaction (see, e.g., Xiong and Seela (2011), J. Org. Chem. 76(14): 5584-5597, incorporated by reference herein in its entirety). In some embodiments, the click reaction is a template-dependent reaction or template-directed reaction. In some embodiments, the template-dependent reaction is sensitive to base pair mismatches such that reaction rate is significantly higher for matched versus unmatched templates. In some embodiments, the click reaction is a nucleophilic addition template-dependent reaction. In some embodiments, the click reaction is a cyclopropane-tetrazine template-dependent reaction.

In some embodiments, the ligation involves enzymatic ligation. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, ligated probe, strand of a selector probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the method comprises using a circular or circularizable construct hybridized to the target nucleic acid comprising the region of interest to generate a product (e.g., comprising an insertion sequence and/or a sequence of the region of interest or one or more barcode sequences associated with the target nucleic acid). In some embodiments, the circular or circularizable construct is circularized using a selector probe as a template. In some aspects, the product is generated using RCA. In any of the embodiments herein, the method can comprise ligating the ends of a circularizable probe hybridized to the target RNA to form a circularized probe. In some embodiments, the method comprises ligating a first and second part of a templated ligation probe hybridized to the target RNA to generate a ligated probe, and ligating the ends of the ligated probe to an insertion sequence using a first strand of a selector probe as a template, thereby forming a circularized probe. In any of the embodiments herein, the method can further comprise generating a rolling circle amplification product of the circularized probe. In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In any of the embodiments herein, the method can further comprise detecting a signal associated with the rolling circle amplification product in the biological sample. In some embodiments, a ligation product of a first and second probe is generated. In some aspects, the ligation product or a derivative thereof (e.g., extension product) can be detected. In some cases, RCA is not performed.

In some embodiments, the circular construct is formed using ligation. In some embodiments, the circular construct is formed using template primer extension followed by ligation. In some embodiments, the circular construct is formed by providing an insertion sequence between ends to be ligated (e.g., using a selector probe as described in Section III). In some embodiments, the circular construct is formed using a combination of any of the foregoing. In some embodiments, the ligation is a DNA-DNA templated ligation. In some embodiments, the ligation is an RNA-RNA templated ligation. In some embodiments, the ligation is a RNA-DNA templated ligation. In some embodiments, a splint is provided as a template for ligation.

In some embodiments, the circular construct is directly hybridized to the target nucleic acid. In some embodiments, the circular construct is formed from a probe or probe set capable of DNA-templated ligation. In some embodiments, the circular construct is formed from a probe or probe set capable of RNA-templated ligation. In some embodiments, the circular construct is formed from a ligation product of nucleic acids probes and/or probe sets described in Section III.

The nature of the ligation reaction depends on the structural components of the polynucleotides used to form the padlock or circular probe. In one embodiment, the polynucleotides comprise complementary docking regions that self-assemble the two or more polynucleotides into a circularized probe that is either ready for ligation because no gaps exist between the docking regions, or is ready for a fill-in process, which will then permit the ligation of the polynucleotides to form the circularized probe. In another embodiment, the docking regions are complementary to a splint.

In some embodiments, a 3' end and a 5' end of the circularizable probe or probe set can be ligated using the target nucleic acid (e.g., RNA) as a template. In some embodiments, the 3' and 5' ends that are ligated using the target nucleic acid as a template are ends of a first part and a second part of a ligatable probe. In some embodiments, the first part and the second part are ligated to generate a ligated probe, and the ligated probe is circularized using a first strand of a selector probe as a template. In some embodiments, the 3' end and the 5' end are ligated without gap filling prior to ligation. In some embodiments, the ligation of the 3' end and the 5' end is preceded by gap filling. The gap may be 1, 2, 3, 4, 5, or more nucleotides.

In some embodiments, the circularizing step may comprise ligation selected from the group consisting of enzymatic ligation, chemical ligation, template dependent ligation, and/or template independent ligation. In any of the embodiments herein, the ligation can comprise using a ligase having an RNA-templated DNA ligase activity and/or an RNA-templated RNA ligase activity. In any of the embodiments herein, the ligation can comprise using a ligase selected from the group consisting of a *Chlorella* virus DNA ligase (PBCV DNA ligase), a T4 RNA ligase, a T4 DNA ligase, and a single-stranded DNA (ssDNA) ligase. In any of the embodiments herein, the ligation can comprise using a PBCV-1 DNA ligase or variant or derivative thereof and/or a T4 RNA ligase 2 (T4 Rnl2) or variant or derivative thereof.

In some embodiments, the method can further comprise prior to the circularizing step, a step of removing molecules of the circularizable probe or probe set (e.g., a first part and a second part of a templated ligation probe that can be circularized using a selector probe as a template) that are not bound to the target nucleic acid from the biological sample. In any of the embodiments herein, the method can further comprise prior to the circularizing step and/or prior to the templated ligation step (e.g., the target nucleic acid templated ligation), a step of removing molecules of the circularizable probe or probe set that are bound to the target nucleic acid but comprise one or more mismatches in the interrogatory sequence from the biological sample. In any of the embodiments herein, the method can further comprise prior to the circularizing step, a step of allowing circularizable probe molecules that are bound to the target nucleic acid but comprise one or more mismatches in the interrogatory sequence to dissociate from the target nucleic acid, while circularizable probe molecules comprising no mismatch in the interrogatory sequence remain bound to the target nucleic acid. In any of the embodiments herein, under the same conditions, the molecules comprising one or more mismatches can be less stably bound to the target nucleic acid than the molecules comprising no mismatch in the interrogatory sequence. In any of the embodiments herein, the method can comprise one or more stringency washes. For instance, one or more stringency washes can be used to remove circularizable probe molecules that are not bound to the target nucleic acid, and/or circularizable probe molecules that are bound to the target nucleic acid but comprise one or more mismatches in the interrogatory sequence.

Following formation of the circularized ligated probe, in some instances, an amplification primer is added. In other instances, the amplification primer is added with the templated ligation probes. In some instances, the amplification primer is the first strand of the selector probe. In some instances, the amplification primer may also be complementary to the target nucleic acid and the circularized probe (e.g., an anchor primer). In some embodiments, the amplification primer may be complementary to all or a portion of the insertion sequence. In some embodiments, a washing step is performed to remove any unbound probes, primers, etc. In some embodiments, the wash is a stringency wash. Washing steps can be performed at any point during the process to remove non-specifically bound probes, probes that have ligated, etc. In some embodiments, the stringency is increased in the hybridization of the probe or probe set to the target nucleic acid, reducing or negating the need of performing a stringency wash.

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. In some embodiments, a primer extension reaction is a reaction where two nucleic acid sequences become linked (e.g., hybridized) by an overlap of their respective terminal complementary nucleic acid sequences (for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set (e.g., a circularized probe comprising an insertion sequence of a selector probe). In some embodiments, the amplifying is achieved by performing rolling circle amplification (RCA). In some embodiments, a strand of the selector probe is used as a primer for amplification. In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Examples of techniques for rolling circle amplification (RCA) include linear RCA, a branched RCA, a dendritic RCA, or any combination thereof (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49(11): 2540-2550; Schweitzer et al. Proc. Natl Acad. Sci. USA 97:101 13-119, 2000; Faruqi et al, BMC Genomics 2:4, 2000; Nallur et al, Nucl. Acids Res. 29:e118, 2001; Dean et al. Genome Res. 11:1095-1099, 2001; Schweitzer et al, Nature Biotech. 20:359-365, 2002; U.S. Pat. Nos. 6,054,274, 6,291,187, 6,323,009, 6,344,329 and 6,368,801, all of which are herein incorporated by reference in their entireties). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some aspects, the polynucleotides and/or amplification product (e.g., amplicon) can be anchored to a polymer matrix. In some embodiments, the selector probe can be anchored to the polymer matrix. In some cases, the anchoring is via a linker (e.g., a 5' linker). For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, U.S. Ser. No. 10/138,509B2, U.S. Ser. No. 10/266, 888B2, US 2016/0024555, US 2018/0251833 and US 2017/0219465, all of which are herein incorporated by reference in their entireties. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

Upon addition of a DNA polymerase in the presence of appropriate dNTP precursors and other cofactors, the amplification primer is elongated by replication of multiple copies of the template (e.g., a concatemer of the template is generated). This amplification product can be detected using, e.g., the secondary and higher order probes and detection oligonucleotides described herein. In some embodiments, the sequence of the amplicon or a portion thereof, is determined or otherwise analyzed, for example by using detectably labeled probes and imaging. The sequencing or analysis of the amplification products can comprise sequencing by hybridization, sequencing by ligation, and/or fluorescent in situ sequencing, and/or wherein the in situ hybridization comprises sequential fluorescent in situ hybridization. In some instances, sequencing using, e.g., the secondary and higher order probes and detection oligonucleotides described herein.

In any of the embodiments herein, the method can further comprise generating the product of the circularized probe in situ in the biological sample. In any of the embodiments herein, the product can be generated using rolling circle amplification (RCA). In any of the embodiments herein, the RCA can comprise a linear RCA, a branched RCA, a dendritic RCA, or any combination thereof. In any of the embodiments herein, the product can be generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

In any of the embodiments herein, the product can be immobilized in the biological sample. In any of the embodiments herein, the product can be crosslinked to one or more other molecules in the biological sample.

In some embodiments, an exemplary workflow for analyzing a biological sample, comprises contacting the biological sample with a probe, wherein: the probe comprises a hybridization region that hybridizes to a target RNA in the biological sample; the hybridization region on the probe comprises an interrogatory region complementary to a region of interest in the target RNA, wherein a second molecule of the target RNA comprises a mismatch with the interrogatory nucleotide; and hybridization between the hybridization region on the probe and the region of interest on the target nucleic acid is blocked by a blocking strand that is hybridized to the hybridization region on the probe or the region of interest on the target nucleic acid. In some embodiments, the method further comprises allowing the probe or a portion thereof (e.g., the hybridization region) to dissociate from the second molecule of the target RNA, wherein under the same conditions, the circularizable probe (e.g., including the hybridization region) remains hybridized to the first molecule of the target RNA. In some embodiments, the method further comprises ligating the ends of the probe hybridized to the first molecule of the target RNA to form a circularized probe; generating a rolling circle amplification product of the circularized probe; and detecting a signal associated with the rolling circle amplification product in the biological sample. In any of the preceding embodiments, the probe hybridized to the second molecule of the target RNA can be destabilized and/or removed from the biological sample while the probe remains hybridized to the first molecule of the target RNA, such that a circularized probe hybridized to the second molecule of the target RNA is not formed. In any of the preceding embodiments, a signal associated with the second molecule of the target RNA may not be detected, such that a signal associated with the rolling circle amplification product is indicative of the first molecule and not the second molecule of the target RNA in the biological sample.

V. Detection and Analysis

In some aspects, after formation of a hybridization complex comprising nucleic acid probes and/or probe sets (e.g., templated ligation probe sets and selector probes) described in Section III and further processing (e.g., ligation, extension amplification, capture, or any combination thereof) as described in Section IV, the method further includes detection of the probe or probe set hybridized to the target nucleic acid or any products generated therefrom or a derivative thereof. In any of the embodiments herein, the method can further comprise imaging the biological sample to detect a ligation product or a circularized probe or product thereof. In any of the embodiments herein, a sequence of the ligation product, rolling circle amplification product, or other generated product can be analyzed in situ in the biological sample. In any of the embodiments herein, the imaging can comprise detecting a signal associated with a fluorescently labeled probe that directly or indirectly binds to a rolling circle amplification product of the circularized probe. In any of the embodiments herein, the sequence of the sequence of the ligation product, rolling circle amplification product, or other generated product can be analyzed by sequential hybridization, sequencing by hybridization, sequencing by ligation, sequencing by synthesis, sequencing by binding, or a combination thereof. In some cases, a barcoded analyte (or a product or derivative thereof) can be released from an array prior to analysis.

The sequencing primer, a ligation product comprising the sequencing primer binding sequence generated in SBL, or a product after one or more cycles of SBL, may be cleaved and/or stripped, for example, prior to one or more subsequent cycles of SBL. A new primer may be hybridized to the insertion sequence or complement thereof and can be reset (relative to a previous sequencing primer) at a position that is offset by one or more nucleotides (in 5' to 3', 3' to 5', or both directions) prior to performing one or more additional cycles of SBL.

In some embodiments, each detection probe (e.g., sequencing probe) comprises an interrogatory nucleotide or sequence (e.g., dinucleotides as shown in the figures) and a sequence of one or more degenerate (N) nucleotides and/or universal nucleotides (Z). As shown in FIG. 3B, in some embodiments, the detection probe comprises a cleavage site, and a cleavage agent can be used to cleave at least the detectable label from the end of the detection probe, thereby regenerating a 5' phosphate. Although the figure depicts the detection probe comprises three degenerate nucleotides and three universal nucleotides, the detection probes can comprise any suitable number of degenerate and/or universal nucleotides (e.g., between 2 and 10, between 2 and 8, or between 3 and 6).

In some embodiments, provided herein are methods including a sequencing-by-ligation (SBL) reaction. In some embodiments of any of the methods for decoding a barcode described herein, the method includes sequencing-by-ligation reaction. In some examples, the SBL reaction includes contacting the sample with a plurality of detection probes, wherein each detection probe comprises an interrogatory region and a detectable label, and is configured to hybridize to the nucleic acid adjacent to an end of the anchor; ligating a detection probe complementary to the first region of interest to the end of the anchor to generate a ligation product; and detecting a signal associated with the detectable label of the ligation product.

Sequencing-by-ligation protocols and other sequencing methods have been described, for example, in US20220042090A1, and U.S. Pat. Nos. 6,306,597, 5,750,341, 5,969,119, 7,906,285, and 9,404,155, the contents of each of which are herein incorporated by reference in their entireties. In traditional sequencing-by-ligation (SBL), for example, three mismatched interrogating (or "sequencing") probes and one correctly matched interrogating probe compete for the same ligation site. The difference in their Tm is generally ~1-2° C., enabling them to equilibrate freely depending on the reaction temperature. The three mismatched interrogating probes and one correctly matched interrogating probe can have different Tm temperatures based on the presence or absence of a matching nucleotide. The level of probe hybridization is a function of probe Tm, which is a function of their length; while the slight difference in the probe melting temperature can be used to discriminate alleles (e.g. allele-specific PCR, allele-specific FISH), the fraction of correctly hybridized probes vary dramatically even with small changes in the reaction temperature. However, in some examples the slight difference in the hybridization rate is insufficient to discriminate individual bases with high specificity. Without being bound by theory, the use of ligase can increase the specificity of the method because the ligase is slow to ligate nicked DNA strands if it recognizes a base-pair mismatch. This dramatically improves the specificity of allele discrimination. Thus, sequencing-by-ligation can involve competitive ligation, rapid equilibration of competing probes, and large difference between correct and mismatched probe ligation, enabling specific determination of a sequence in a region of interest. Numerous variations of sequencing-by-ligation are possible and can be used in a method disclosed herein.

In some embodiments, SBL detection probes are labelled with an optical label. In other embodiments, SBL detection probes comprise alternative labels, such a barcode label that allows discrimination of SBL detection probes using probe hybridization, antibody-based detection, or any other means of affinity-based detection.

In some embodiments, SBL detection probes comprise cleavable terminators. Cleavable terminators can prevent simultaneous ligation of multiple SBL probes on repetitive sequences. Cleavable terminators can include, for example, Endonuclease V-based cleavage of DNA. Endonuclease V cuts the DNA 2 or 3 bases away from inosine; therefore, phosphorothioate groups can be added to define the cleavage site at a desired position. This results in efficient cleavage of the terminator to generate a cleaved fragment, which optionally comprises the detectable label.

In some embodiments, the ligase is capable of performing RNA-splinted ligation. In some embodiments, the ligase is a PBCV ligase (e.g., *Chlorella* Virus PBCV-1). In some embodiments, the ligase is T4 Rnl2. In some embodiments, the ligase is a T4 DNA ligase.

In any of the embodiments herein, a sequence associated with the target nucleic acid or the probe(s) can comprise one or more barcode sequences or complements thereof. In any of the embodiments herein, the sequence of the rolling circle amplification product can comprise one or more barcode sequences or complements thereof. In any of the embodiments herein, a ligated first-second probe can comprise one or more barcode sequences or complements thereof. In any of the embodiments herein, the one or more barcode sequences can comprise a barcode sequence corresponding to the target nucleic acid. In any of the embodiments herein, the one or more barcode sequences can comprise a barcode sequence corresponding to the sequence of interest, such as variant(s) of a single nucleotide of interest. In some embodiments, "Insertion" or "overhang" barcode sequence refers the location of a barcode sequence (e.g., comprised by the insertion sequence or an overhang of the templated ligation probe), and can otherwise be considered equivalent and/or used interchangeably with the term "barcode sequence" as described above.

In any of the embodiments herein, the detecting step can comprise contacting the biological sample with one or more detectably-labeled probes that directly or indirectly hybridize to the rolling circle amplification product, and dehybridizing the one or more detectably-labeled probes from the rolling circle amplification product. In any of the embodiments herein, the contacting and dehybridizing steps can be repeated with the one or more detectably-labeled probes and/or one or more other detectably-labeled probes that directly or indirectly hybridize to the rolling circle amplification product.

In any of the embodiments herein, the detecting step can comprise contacting the biological sample with one or more intermediate probes that directly or indirectly hybridize to the rolling circle amplification product, wherein the one or more intermediate probes are detectable using one or more detectably-labeled probes. In any of the embodiments herein, the detecting step can further comprise dehybridizing the one or more intermediate probes and/or the one or more detectably-labeled probes from the rolling circle amplification product. In any of the embodiments herein, the contacting and dehybridizing steps can be repeated with the one or more intermediate probes, the one or more detectably-labeled probes, one or more other intermediate probes, and/or one or more other detectably-labeled probes.

In some embodiments, the one or more intermediate probes comprise one or more overhang regions (e.g., a 5' and/or 3' end of the probe that does not hybridize to the rolling circle amplification product). A probe comprising a single overhang region may be referred to as an "L-shaped probe," and a probe comprising two overhangs may be referred to as a "U-shaped probe." In some cases, the overhang region comprises a binding region for binding one or more detectably-labeled probes. In some embodiments, the detecting comprises contacting the biological sample with a pool of intermediate probes corresponding to different barcode sequences or portions thereof, and a pool of detectably-labeled probes corresponding to different detectable labels. In some embodiments, the biological sample is sequentially contacted with different pools of intermediate probes. In some instances, a common or universal pool of detectably-labeled probes is used in a plurality of sequential hybridization steps (e.g., with different pools of intermediate probes).

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the primary probes, secondary probes, higher order probes, and/or detectably labeled probes may comprise any of a variety of entities able to hybridize a nucleic acid, e.g., DNA, RNA, LNA, and/or PNA, etc., depending on the application.

In some embodiments, disclosed herein is a multiplexed assay where multiple targets (e.g., nucleic acids such as genes or RNA transcripts, or protein targets) are probed with multiple primary probes (e.g., circularizable primary probes, such as a templated ligation probe that can be circularized using a selector probe as a template), and optionally multiple secondary probes hybridizing to the primary barcodes (or complementary sequences thereof) are all hybridized at once, followed by sequential secondary barcode detection and decoding of the signals. In some embodiments, detection of barcodes or subsequences of the barcode can occur in a cyclic manner.

In some embodiments, a method for analyzing a region of interest in a target nucleic acid is a multiplexed assay where multiple probes (e.g., circularizable probes, such as a templated ligation probe that can be circularized using a selector probe as a template) are used to detect multiple regions of interest simultaneously (e.g., variations at the same location of a target nucleic acid and/or SNPs in various locations). In some embodiments, one or more detections of one or more regions of interest may occur simultaneously. In some embodiments, one or more detections of one or more regions of interest may occur sequentially. In some embodiments, multiple circularizable probes of the same circularizable probe design are used to detect one or more regions of interest, using different barcodes associated with each region of interest. In some embodiments, multiple circularizable probes of different circularizable probe design are used to detect one or more regions of interest, using different barcodes (e.g., each barcode associated with a target nucleic acid or sequence thereof). In some embodiments, the one or more regions of interest are localized on the same molecule (e.g., RNA or DNA). In alternative embodiments, the one or more single nucleotides of interest are localized on different molecules.

In some aspects, the provided methods involve analyzing, e.g., detecting or determining, one or more sequences present in the polynucleotides (e.g., probe or probe set) and/or in a product or derivative thereof, such as in an amplified circular or circularized probe. In some embodiments, the detection comprises providing detection probes, such as probes for performing a chain reaction that forms an amplification product, e.g., HCR. In some embodiments, the analysis comprises determining the sequence of all or a portion of the amplification product. In some embodiments, the analysis comprises detecting a sequence present in the amplification product. In some embodiments, the sequence of all or a portion of the amplification product is indicative of the identity of a region of interest in a target nucleic acid. In other embodiments, the provided methods involve analyzing, e.g., detecting or determining, one or more sequences present in the polynucleotide probes (e.g., a barcode sequence present in a circularized probe or product thereof).

In some embodiments, a method disclosed herein may also comprise one or more signal amplification components. In some embodiments, the present disclosure relates to the detection of nucleic acids sequences in situ using probe hybridization and generation of amplified signals associated with the probes, wherein background signal is reduced and sensitivity is increased. In some embodiments, the RCA product generated using a method disclosed herein can be detected in with a method that comprises signal amplification.

Exemplary signal amplification methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, US20190376956A1, US20220026433A1, US20220128565A1, and US20210222234A1, all of which are incorporated herein by reference in their entireties.

In some embodiments, hybridization chain reaction (HCR) can be used for signal amplification. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28(11), 1208-1212; and Song et al, 2012, Analyst, 137, 1396-1401), all of which are herein incorporated by reference in their entireties. HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described (see, e.g., US20220064697A1 incorporated herein by reference), and may be used in the methods herein.

In some embodiments, similar to HCR reactions that use hairpin monomers, linear oligo hybridization chain reaction (LO-HCR) can also be used for signal amplification. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. In any of the embodiments herein, the target nucleic acid molecule and/or the analyte can be an RCA product.

In some embodiments, detection of nucleic acids sequences in situ includes combination of RCA with an assembly for branched signal amplification. In some embodiments, the assembly complex comprises an amplifier hybridized directly or indirectly (via one or more oligonucleotides) to a sequence of the RCA product. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some embodiments, the RCA product can be detected in with a method that comprises signal amplification by performing a primer exchange reaction (PER). In various embodiments, a primer with domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising RCA products generated using methods described herein. In various embodiments, the RCA product may be contacted with a plurality of concatemer primers and a plurality of labeled probes. see e.g., U.S. Pat. Pub. No. US20190106733, which is incorporated herein by reference, for exemplary molecules and PER reaction components.

In some embodiments, the methods comprise sequencing all or a portion of the amplification product, such as one or more barcode sequences present in the amplification product.

In some embodiments, the product or derivative of a first and second probe ligated together after hybridizing to the target nucleic acid can be analyzed by sequencing. In some embodiments, the analysis and/or sequence determination comprises sequencing all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the analysis and/or sequence determination comprises detecting a polymer generated by a hybridization chain reaction (HCR) reaction, see e.g., US 2017/0009278, which is incorporated herein by reference, for exemplary probes and HCR reaction components. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the polynucleotides, for example, via binding of the detection probe and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa dyes, fluorescein, YPet, CyPet, Cascade blue, allophycocyanin, Cy3, Cy5, Cy7, rhodamine, dansyl, umbelliferone, Texas red, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (MaxVision Biosciences), and/or a very intense black dye (e.g., Sudan Black, or comparable dark chromophore).

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}I$, $^{35}S$, $^{14}C$, or $^{3}H$. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes), all of which are herein incorporated by reference in their entireties. Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264, all of which are herein incorporated by reference in their entireties. In some embodiments, the fluorescent label comprises a signaling moiety that conveys information through the fluorescent absorption and/or emission properties of one or more molecules. Exemplary fluorescence properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy3-dCTP, Cy3-dUTP, Cy5-dCTP, Cy5-dUTP (Amersham Biosciences, Piscataway, N.J.), fluorescein-!2-dUTP, tetramethylrhodamine-6-dUTP, TEXAS RED™-5-dUTP, CASCADE BLUE™-7-dUTP, BODIPY TMFL-14-dUTP, BODIPY TMR-14-dUTP, BODIPY TMTR-14-dUTP, RHOD AMINE GREEN™-5-dUTP, OREGON GREENR™ 488-5-dUTP, TEXAS RED™-12-dUTP, BODIPY™ 630/650-14-dUTP, BODIPY™ 650/665-14-dUTP, ALEXA FLUOR™ 488-5-dUTP, ALEXA FLUOR™ 532-5-dUTP, ALEXA FLUOR™ 568-5-dUTP, ALEXA FLUOR™ 594-5-dUTP, ALEXA FLUOR™ 546-14-dUTP, fluorescein-12-UTP, tetramethylrhodamine-6-UTP, TEXAS RED™-5-UTP, mCherry, CASCADE BLUE™-7-UTP, BODIPY™ FL-14-UTP, BODIPY TMR-14-UTP, BODIPY™ TR-14-UTP, RHOD AMINE GREEN™-5-UTP, ALEXA FLUOR™ 488-5-UTP, and ALEXA FLUOR™ 546-14-UTP (Molecular Probes, Inc. Eugene, Oreg.). Methods for custom synthesis of nucleotides having other fluorophores such as disclosed in Henegariu et al. (2000) Nature Biotechnol. 18:345.

Other fluorophores available for post-synthetic attachment comprise, but are not limited to, ALEXA FLUOR™ 350, ALEXA FLUOR™ 532, ALEXA FLUOR™ 546, ALEXA FLUOR™ 568, ALEXA FLUOR™ 594, ALEXA FLUOR™ 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethyl rhodamine, Texas Red (available from Molecular Probes, Inc., Eugene, Oreg.), Cy2, Cy3.5, Cy5.5, and Cy7 (Amersham Biosciences, Piscataway, N.J.). FRET tandem fluorophores may also be used, comprising, but not limited to, PerCP-Cy5.5, PE-Cy5, PE-Cy5.5, PE-Cy7, PE-Texas Red, APC-Cy7, PE-Alexa dyes (610, 647, 680), and APC-Alexa dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. In some embodiments, the antibody is an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 91/17160, all of which are herein incorporated by reference in their entireties. Many different hapten-capture agent pairs are available for use. Exemplary haptens comprise, but are not limited to, biotin, des-biotin and other derivatives, dinitrophenol, dansyl, fluorescein, Cy5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity—so long exposures are often required. As only one point in the sample is illuminated at a time, 2D or 3D imaging requires scanning over a regular raster (e.g., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning possible makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunostained tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECS™), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSTM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (e.g., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) Anal. Biochem. 320, 55-65, and Lee et al., (2014) Science, 343(6177), 1360-1363. In addition, examples of methods and systems for performing in situ sequencing are described in US 2016/0024555, US 2019/0194709, and in U.S. Pat. Nos. 10,138,509, 10,494,662 and 10,179,932, all of which are herein incorporated by reference in their entireties. Exemplary techniques for in situ sequencing or sequence detection comprise, but are not limited to, STARmap (described for example in Wang et al., (2018) Science, 361(6499) 5691), MERFISH (described for example in Moffitt, (2016) Methods in Enzymology, 572, 1-49), hybridization-based in situ sequencing (HybISS) (described for example in Gyllborg et al., Nucleic Acids Res (2020) 48(19):e112, and FISSEQ (described for example in US 2019/0032121), all of which are herein incorporated by reference in their entireties. In some cases, sequencing can be performed after the analytes are released from the biological sample.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232, all of which are herein incorporated by reference in their entireties.

In some embodiments, sequence analysis of nucleic acids (e.g., nucleic acids such as probes or RCA products comprising barcode sequences) can be performed by sequential hybridization (e.g., sequencing by hybridization and/or sequential in situ fluorescence hybridization). Sequential fluorescence hybridization can involve sequential hybridization of detectable probes comprising an oligonucleotide and a detectable label. In some embodiments, a method disclosed herein comprises sequential hybridization of the detectable probes disclosed herein, including detectably labeled probes (e.g., fluorophore conjugated oligonucleotides) and/or probes that are not detectably labeled per se but are capable of binding (e.g., via nucleic acid hybridization) and being detected by detectably labeled probes. Exemplary methods comprising sequential fluorescence hybridization of detectable probes are described in US 2019/0161796, US 2020/0224244, US 2022/0010358, US 2021/0340618, and WO 2021/138676, all of which are incorporated herein by reference. In some embodiments, the methods provided herein can include analyzing the identifier sequences (e.g., analyte sequences or barcode sequences) by sequential hybridization and detection with a plurality of labeled probes (e.g., detection oligonucleotides).

In some embodiments, sequence detection comprises contacting the biological sample with one or more intermediate probes that directly or indirectly hybridize to a rolling circle amplification product, wherein the one or more intermediate probes are detectable using one or more detectably-labeled probes, and dehybridizing the one or more intermediate probes and/or the one or more detectably-labeled probes from the rolling circle amplification product. In some embodiments, the one or more intermediate probes comprise one or more overhang regions (e.g., a 5' and/or 3' end of the probe that does not hybridize to the rolling circle amplification product), such as an "L-shaped probe" and/or a "U-shaped probe," and each overhang region can comprise a binding region for binding one or more detectably-labeled probes.

In some embodiments, provided herein are methods for in situ analysis of analytes in a sample using sequential probe hybridization. In some aspects provided herein is a method for analyzing a biological sample, comprising: a) generating a rolling circle amplification product (RCP) of a circularizable probe or probe set described herein, the RCP comprising an identifier sequence such as a barcode sequence or analyte sequence, wherein the identifier sequence is associated with an analyte of interest and is assigned a signal code sequence; b) contacting the biological sample with a first probe (e.g., an intermediate probe such as an L-probe) and a first detectably labeled probe to generate a first complex comprising the first probe hybridized to the RCP and the first detectably labeled probe hybridized to the first probe, wherein the first probe comprises (i) a recognition sequence (e.g., a target-binding sequence) complementary to the identifier sequence (e.g., barcode sequence or analyte sequence) and (ii) a first landing sequence (e.g., an overhang sequence), and wherein the first detectably labeled probe comprises a sequence complementary to the first landing sequence; c) detecting a first signal associated with the first detectably labeled probe, wherein the first signal corresponds to a first signal code in the signal code sequence; d) contacting the biological sample with a second probe (e.g., an intermediate probe such as L-probe) and a second detectably labeled probe to generate a second complex comprising the second probe hybridized to the RCP and the second detectably labeled probe hybridized to the second probe, wherein the second probe comprises (i) a recognition sequence (e.g., a target-binding sequence) complementary to the identifier sequence (e.g., barcode sequence or analyte sequence) and (ii) a second landing sequence (e.g., an overhang sequence), and wherein the second detectably labeled probe comprises a sequence complementary to the second landing sequence; and e) detecting a second signal associated with the second detectably labeled probe, wherein the second signal corresponds to a second signal code in the signal code sequence, wherein the signal code sequence comprising the first signal code and the second signal code is determined at a location in the biological sample, thereby decoding the identifier sequence (e.g., barcode sequence or analyte sequence) and identifying the analyte of interest at the location in the biological sample. In some embodiments, the detectable label of the first detectably labeled probe and the detectable label of the second detectably labeled probe are the same. In some embodiments, the detectable labels of the first detectably labeled probe and the second detectably labeled probe are different. In some embodiments, the first signal code and the second signal code are the same. In some embodiments, the first signal code and the second signal code are different.

In some embodiments, the first probe (e.g., a first intermediate probe such as a first L-probe), the second probe (e.g., a second intermediate probe such as a second L-probe), and one or more subsequent probes (e.g., subsequent intermediate probe such as subsequent L-probes) are contacted with the biological sample sequentially in a predetermined sequence which corresponds to the signal code sequence assigned to the identifier sequence (e.g., barcode sequence or analyte sequence), wherein the one or more subsequent probes each comprises (i) a recognition sequence complementary to the identifier sequence (e.g., barcode sequence or analyte sequence) and (ii) an overhang sequence complementary to a detectably labeled probe of a pool (e.g., a universal pool across different cycles of probe hybridization) of detectably labeled probes. In some embodiments, the biological sample is contacted with the first probe before the second probe and one or more subsequent probes. In some embodiments, the biological sample is contacted with the second after the first probe and before and one or more subsequent probes. In some embodiments, the biological sample is contacted with the one or more subsequent probes after the first probe. In some embodiments, the biological sample is contacted with the one or more subsequent probes after the first probe and the second probe.

In some embodiments, the first detectably labeled probe and the second detectably labeled probe are in the pool of detectably labeled probes. A pool of detectably labeled probes may comprises at least two detectably labeled probes, and may be used for multiplexing analyses of two or more target analytes (e.g., target nucleic acids) in a biological sample. In some embodiments, the contacting in b) comprises contacting the biological sample with the universal pool of detectably labeled probes, and the contacting in d) comprises contacting the biological sample with the universal pool of detectably labeled probes. In some embodiments, the universal pool of detectably labeled probes used in the contacting in b) is the same as the universal pool of detectably labeled probes used in the contacting in d). In some embodiments, the universal pool comprises detectably labeled probes each having a detectable label corresponding to a different nucleic acid sequence for hybridization to a landing sequence (e.g., an overhang sequence) in a probe (e.g., an intermediate probe such as an L-probe). In some embodiments, the number of different detectably labeled probes in the universal pool is four.

In some embodiments, the one or more subsequent probes are contacted with the biological sample to determine signal codes in the signal code sequence until sufficient signal codes have been determined to decode the identifier sequence (e.g., barcode sequence or analyte sequence), thereby identifying the target analyte (e.g., target nucleic acid). In some embodiments, the method further comprises a step of removing the first probe and/or the first detectably labeled probe from the biological sample before contacting the sample with a subsequent probe and a detectably labeled probe hybridizing to the subsequent probe. In some embodiments, the method further comprises a step of removing the second probe and/or the second detectably labeled probe from the biological sample, before contacting the sample with a subsequent probe and a detectably labeled probe hybridizing to the subsequent probe.

In some embodiments, the method further comprises identifying multiple different target analytes present at locations (e.g., different locations) in the biological sample. In some embodiments, each different target analyte is assigned a different signal code sequence and is targeted by a circularizable probe or probe set comprising a complement of a different barcode sequence of the plurality of barcode sequences. In some embodiments, the number of different probes (e.g., L-probes that have different recognition sequences that bind to the barcode sequences) in each pool of probes is greater than the number of different detectably labeled probes in the universal pool of detectably labeled probes. In some embodiments, the number of different detectably labeled probes in the universal pool is four. In some embodiments, the number of different probes in each pool of probes (e.g., L-probes) is about 10, about 20, about 30, about 40, about 50, about 100, about 200, about 500, about 1,000, or more. In some embodiments, the number of different recognition sequences (e.g., recognition sequences that bind to the barcode sequences) of probes in each pool of probes in at least about 10, such as at least any of about 20, 30, 40, 50, 100, 200, 500, 1,000, or more.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309: 1728-1732, and in U.S. Pat. Nos. 5,599,675; 5,750,341; 6,969,488; 6,172,218; and 6,306,597, all of which are herein incorporated by reference in their entireties.

In some embodiments, the barcodes of the probes (e.g., the ligation product or the circularized ligation product comprising the insertion sequence, e.g., as shown in FIG. 1 or FIG. 2) or complements or products thereof are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568(7751):235-239 (2019); Chen et al., *Science;* 348(6233):aaa6090 (2015); Gyllborg et al., Nucleic Acids Res (2020) 48(19):e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004), all of which are herein incorporated by reference in their entireties.

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181, all of which are herein incorporated by reference in their entireties.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

VI. Compositions and Kits

In some aspects, disclosed herein is a composition that comprises a complex containing a target nucleic acid and one or more probes (e.g., a templated ligation probe and a selector probe). The probes are any as described herein. In some embodiments, the composition comprises a templated ligation probe comprising a first part and a second part, and a selector probe. In some embodiments, the composition comprises a target nucleic acid, a templated ligation probe comprising a first part and a second part, and a selector probe. In some embodiments, the composition comprises a target nucleic acid or multiple target nucleic acids and a circular probe formed using any of the templated ligation probes and selector probes described herein. In some embodiments, the composition further includes an anchor or an additional primer for amplification of the circular probe. In some embodiments, the composition comprises a target nucleic acid or multiple target nucleic acids and an amplification product of the circular probe.

Also provided herein are kits comprising one or more probes (e.g., templated ligation probes, selector probes, and optionally detection probes for detecting an amplification product of a circularized probe), including any as described in Section III, and reagents for performing the methods provided herein, for example reagents required for one or more steps comprising hybridization, ligation, amplification, detection, sequencing, and/or sample preparation as described herein. In some embodiments, the kit comprises a) a first and second probe (e.g., DNA probes) each comprising a target specific binding site which is complementary to a cognate probe-binding site at or adjacent to a region of interest in a target RNA, and b) a selector probe comprising a first strand and a second strand that form a partially double stranded probe, wherein the first strand comprises a first homology arm complementary to a first end of the region of interest, a second homology arm complementary to a second end of the region of interest, and a region that hybridizes to the second strand, and wherein the second strand comprises an insertion sequence.

In some embodiments, the kit further comprises a target nucleic acid. In some embodiments, any or all of the polynucleotides are DNA molecules. In some embodiments, the target nucleic acid is a messenger RNA molecule. In some embodiments, the kit further comprises a ligase, for instance for forming a ligated circular probe from the probes and/or oligonucleotides. In some embodiments, the ligase has DNA-splinted DNA ligase activity. In some embodiments, the ligase has DNA- or RNA-splinted RNA ligase activity. In some embodiments, the kit further comprises a polymerase, for instance for performing amplification of the circularizable probe (e.g., a ligated probe that is circularized using the selector probe as a template). In some embodiments, the polymerase is capable of using the circularized ligated probe as a template for amplification. In some embodiments, the kit further comprises an anchor and/or an additional primer for amplification.

In some embodiments, the kit further includes reagents for performing the methods provided herein, for example reagents required for one or more steps comprising hybridization, ligation, amplification, detection, sequencing, and/or sample preparation as described herein. In some embodiments, the kit further comprises a target nucleic acid. In some embodiments, any or all of the templated ligation probes and/or selector probes are DNA molecules. In some embodiments, any or all of the templated ligation probes and/or selector probes comprise RNA. In some embodiments, the target nucleic acid is a messenger RNA molecule. In some embodiments, the kit further comprises a ligase, for instance for forming a ligated circular probe from the probes and/or oligonucleotides. In some embodiments, the ligase has DNA-splinted DNA ligase activity. In some embodiments, the kit further comprises a polymerase, for instance for performing amplification of the circularizable probe. In some embodiments, the polymerase is capable of using the ligated circular probe as a template for amplification. In some embodiments, the kit further comprises a primer for amplification.

In some aspects, provided herein is a kit for generating a circularized ligated probe, comprising: (i) a templated ligation probe comprising a first part and a second part, wherein at least one of the first part and the second part comprises a target specific binding site which is complementary to a cognate probe-binding site at or adjacent to a region of interest in a target nucleic acid, wherein the first part and the second part, respectively, comprise a first hybridization region and second hybridization region cognate to a first and second sequence of the target nucleic acid, such that upon hybridization of the first part and second part to the target nucleic acid ligatable ends of the first and second parts are juxtaposed for ligation to each other using the target nucleic acid as a ligation template to generate a ligated probe; and (ii) a selector probe comprising a first strand and a second strand that form a partially double stranded probe, wherein the first strand comprises a first homology arm complementary to a first end of the ligated probe, a second homology arm complementary to a second end of the ligated probe, and a region that hybridizes to the second strand, and wherein the second strand comprises an insertion sequence.

The first part, second part, and selector probe can be any described herein. In some embodiments, the first part and the second part each comprise an overhang sequence that does not hybridize to the target nucleic acid. In some embodiments, the overhang comprises an adapter region. In some embodiments, the homology arms of the selector probe hybridize to the adapter regions of the ligated probe. In some embodiments, the adapter region is a common adapter region and optionally the insertion sequence is an anchor or primer sequence. Alternatively, in some embodiments, the adapter region corresponds to a sequence of the target nucleic acid and optionally the insertion sequence comprises a barcode sequence corresponding to the target nucleic acid.

In some embodiments, the first part, second part, and/or the selector probe comprise DNA. In some embodiments, the first part, second part, and/or the selector probe comprise RNA. In some embodiments, the first part, second part, and/or the selector probe comprise DNA and RNA.

In some embodiments, the kit comprises a plurality of templated ligation probes as described herein, and a plurality of selector probes as described herein. In some embodiments, each selector probe of the plurality is cognate to a ligation probe of the plurality of ligation probes. In some embodiments, the insertion sequence of a selector probe comprises one or more barcode sequences. In some embodiments, the one or more barcode sequences correspond to (e.g., uniquely correspond to) the region of interest of the target nucleic acid for the cognate ligation probe. In some embodiments, the insertion sequences of a plurality of the selector probes comprise common sequences. In some embodiments, the kit further comprises one or more detection anchor probes complementary to the common sequences (e.g., anchor sequences) or complements thereof. In some embodiments, the kit further comprises one or more sequencing primers complementary to the common sequences (e.g., sequencing primer binding sequences) or complements thereof. In some embodiments, the kit further comprised detection probes for performing sequencing by ligation and/or one or more reagents for performing sequencing-by-ligation.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

VII. Applications

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some embodiments, the region of interest comprises a single-nucleotide polymorphism (SNP). In some embodiments, the region of interest comprises is a single-nucleotide variant (SNV). In some embodiments, the region of interest comprises a single-nucleotide substitution. In some embodiments, the region of interest comprises a point mutation. In some embodiments, the region of interest comprises a single-nucleotide insertion.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

In some aspects, the embodiments can be applied to visualize the distribution of genetically encoded markers in whole tissue at subcellular resolution, for example, chromosomal abnormalities (inversions, duplications, translocations, etc.), loss of genetic heterozygosity, the presence of gene alleles indicative of a predisposition towards disease or good health, likelihood of responsiveness to therapy, or in personalized medicine or ancestry.

VIII. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases can be included in a nucleic acid or nucleotide, such as 7-deazadeoxyadenosine (A1) and 5-chlorodeoxyuridine.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., can be oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

Two nucleic acid sequences can become linked (e.g., hybridized) by an overlap of their respective terminal complementary nucleic acid sequences (for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™ ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™ ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(x) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also refer to an "epitope binding fragment" or "antibody fragment," which generally refers to a portion of a complete antibody capable of binding the same epitope as the complete antibody, albeit not necessarily to the same extent. Although multiple types of epitope binding fragments are possible, an epitope binding fragment typically comprises at least one pair of heavy and light chain variable regions (VH and VL, respectively) held together (e.g., by disulfide bonds) to preserve the antigen binding site, and does not contain all or a portion of the Fc region. Epitope binding fragments of an antibody can be obtained from a given antibody by any suitable technique (e.g., recombinant DNA technology or enzymatic or chemical cleavage of a complete antibody), and typically can be screened for specificity in the same manner in which complete antibodies are screened. In some embodiments, an epitope binding fragment comprises an F(ab')$_2$ fragment, Fab' fragment, Fab fragment, Fd fragment, or Fv fragment. In some embodiments, the term "antibody" includes antibody-derived polypeptides, such as single chain variable fragments (scFv), diabodies or other multimeric scFvs, heavy chain antibodies, single domain antibodies, or other polypeptides comprising a sufficient portion of an antibody (e.g., one or more complementarity determining regions (CDRs)) to confer specific antigen binding ability to the polypeptide.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay, a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labelled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, DiI (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorphyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™1/PO-PRO™-1, POPO™3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO™-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66W, YFP (Yellow Fluorescent Protein), YOYO®-1/YO-PRO®-1, YOYO®-3/ YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. Examples of compound families to provide chemiluminescence under a variety of conditions include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLES

The following example is included for illustrative purposes only and is not intended to limit the scope of the present disclosure.

Example 1: Use of a Templated Ligation Probe and Selector Probe to Detect a Target Nucleic Acid This example describes the design and use of a templated ligation probe (e.g., comprising a first part and a second part) for detecting a target nucleic acid and generating a ligated probe, then circularizing the ligated probe using a selector probe.

A tissue sample is obtained and cryosectioned onto a glass slide for processing. The tissue is fixed by incubating in 3.7% paraformaldehyde (PFA). One or more washes is performed and the tissue is then permeabilized. To prepare for probe hybridization, a wash buffer is added to the tissue section.

A probe set mixture is incubated with the thin tissue section sample and hybridization buffer for hybridization of the probe sets to target nucleic acid (e.g., mRNAs) in the sample. The probe set mixture comprises a first part and a second part of a templated ligation probe, wherein the first part comprises hybridization region HR1 and second part comprises hybridization region HR2 that each hybridize to the target nucleic acid via a hybridization regions HR1' or HR2' respectively. The ends of the first and second part of the templated ligation probe may each comprise an optional overhang as depicted in FIG. 2. The sample is then washed to remove unbound probes and incubated with a ligase for ligation of the juxtaposed ends of the first and second parts to generate a ligated probe. In some embodiments, the ligated probe can be released from the target nucleic acid (e.g., by digestion with RNase H), thus freeing the ends of the ligated probe for the second and third ligation.

After the first ligation, a selector probe comprising a first and second strand is added to the sample. The first strand of the selector probe comprises a first homology arm complementary to a first end of the ligated probe and a second homology arm complementary to a second end of the ligated probe, and a region that hybridizes to the second strand. The selector probe also comprises an insertion sequence as depicted in FIGS. 1 and 2. The sample is optionally washed and then contacted with a ligase mixture to circularize the ligated probe using the selector probe as template, ligating both ends of the ligated probe to the second strand of the selector probe, generating a circular ligated probe including the insertion sequence. For amplification, a primer may be added or the first strand of the selector probe can be used as a primer for amplification of the circular probe. The sample is then incubated with a rolling-circle amplification (RCA) mixture containing a Phi29 DNA polymerase and dNTPs for RCA of the circular probes.

Detection of sequences of the RCA product can be performed using sequencing by synthesis (SBS), sequencing by ligation (SBL), or sequencing by hybridization (SBH). For example, fluorescently labeled oligonucleotides complementary to a portion of the RCA product, a barcode contained therein, or a secondary probe attached thereto are incubated with the sample. Multiple cycles of contacting the sample with probes and sequence determination (e.g., using in situ sequencing based on sequencing-by-ligation or sequencing-by-hybridization) can be performed. Fluorescent images can be obtained in each cycle, and one or more wash steps can be performed in a cycle or between cycles. Probes targeting target nucleic acids can be sequentially or simultaneously provided, processed, and detected as described above.

Example 2: Sequencing Regions Flanking the Insertion Sequence by SBL

This example describes the design and use of a templated ligation probe (e.g., comprising a first part and a second part) for detecting a target nucleic acid and generating a ligated probe, then circularizing the ligated probe using a selector probe to insert an sequencing primer binding sequence for hybridization of a sequencing primer.

A tissue sample is obtained and incubated with templated ligation probes as described above. Optionally, the sample is incubated with a plurality of templated ligation probes for detecting a plurality of target nucleic acids. Optionally, the end of the first part of the templated ligation probe comprises an overhang comprising a first portion of a barcode region, and the end of the second part of the templated ligation probe comprises an overhang comprising a second portion of the barcode region, as shown in FIG. 3A. After the first ligation of the first part and second part of the templated ligation probes to form ligated probes, a selector probe comprising a first and second strand is added to the sample. The first strand of the selector probe comprises a first homology arm complementary to a first end of the ligated probe and a second homology arm complementary to a second end of the ligated probe, and a region that hybridizes to the second strand. The selector probe also comprises an insertion sequence as depicted in FIG. 1, FIG. 2, and FIG.

3A. The insertion sequence or complement thereof can comprise a sequencing primer binding sequence for hybridization of a sequencing primer.

The sample is optionally washed and then contacted with a ligase mixture to circularize the ligated probe using the selector probe as template, ligating both ends of the ligated probe to the second strand of the selector probe, generating a circular ligated probe including the insertion sequence (e.g., the sequencing primer binding sequence). The insertion sequence can be the same for multiple different ligated probes. Rolling circle amplification can be performed as described in Example 1 above to generate an RCA product. In the example wherein an end of the first part comprises a first portion of a barcode region and an end of the second part comprises a second portion of the barcode region as shown in FIG. 3A, the RCA product comprises multiple copies of the complement of the first portion of the barcode region and the second portion of the barcode region flanking the insertion sequence (e.g., sequencing primer binding sequence), as shown in FIG. 3C. In another example wherein the first part and second part are fully hybridized to the target nucleic acid prior to release as shown in FIG. 1, the RCA product comprises multiple copies of the complement of the insertion sequence is flanked by the target specific binding sites of the first and second parts of the templated ligation probe.

After rolling circle amplification, a sequencing primer can be hybridized to the complement of the sequencing primer binding sequence in the RCA product. SBL can be used to analyze a region of interest located 5' to the complement of the insertion sequence that hybridizes to the sequencing primer by ligating detection probes to the 3' end of the sequencing primer, as shown in FIGS. 4A-4B. Similarly, SBL can be used to analyze a region of interest located 3' to the complement of the insertion sequence that hybridizes to the sequencing primer by ligating detection probes to the 5' end of the sequencing primer, as shown in FIGS. 4C-4D. Optionally, the region of interest located 5' to the complement of the insertion sequence is the complement of the first portion of the barcode region, and the region of interest located 3' to the complement of the insertion sequence is the complement of the second portion of the barcode region, as shown in FIGS. 4A-4D.

In some examples, SBL uses a combinatorial sequencing approach, wherein in a first set of detection probes comprise one or more known nucleotides at a first position of the sequencing probe, and a second round of detection probes comprise one or more known nucleotides at a second position of the sequencing probe. The detection probes can also comprise a sequence of one or more degenerate (N) nucleotides and/or universal nucleotides (Z). Each detection probe comprises an optical label corresponding to the known nucleotide or the known sequence of nucleotides.

Ligation of the detection probe to the sequencing primer depends on complementarity of the known nucleotide(s) of the detection probe with the target nucleic acid at the corresponding position (e.g., a known nucleotide in the first position at the 3' end of a detection probe ligated to the 5' end of the sequencing primer must correspond to the nucleotide immediately 3' to the known complement of the insertion sequence, a known nucleotide in the second position at the 3' end of a detection probe ligated to the 5' end of the sequencing primer must correspond to the nucleotide in the second position 3' of the known complement of the insertion sequence, and so on). After ligation of the detection probe to the sequencing primer, an image is obtained of the optical label associated with the first detection probe while the detection probe is hybridized to the region of interest. The nucleotide(s) of the region of interest is/are determined by identifying the complement(s) of the known nucleotide(s) at the known sequence position of the first detection probe.

Prior to hybridization of the second round of detection probes, the first detection probe can be contacted with a nuclease where the nuclease cleaves the first detection probe from the sequencing primer, and the first detection probe can be removed leaving the 5' phosphate of the primer for ligation of the second detection probe. Optionally, a kinase can add a phosphate group to the cleaved first detection probe if the nuclease reaction removes the free 5' phosphate necessary for ligation of the additional sequencing primer. Alternatively, the ligated primer-detection probe complex can be removed and the complement of the sequencing primer sequence can be contacted with a new sequencing primer for ligation to a detection probe of the second round of detection probes.

After ligation of the second detection probe to the sequencing primer, an image is obtained of the optical label associated with the second detection probe while the second detection probe is hybridized to the first region of interest. The nucleotide(s) of the region of interest is/are determined by identifying the complement(s) of the known nucleotide(s) at the known sequence position of the second sequencing probe.

The steps of SBL can be repeated in order to determine the sequence of the region of interest 3' to the complement of the insertion sequence and/or the sequence of the region of interest 5' to the complement of the insertion sequence. Optionally, the steps of SBL can be repeated in order to determine (in any order) the sequence of the complement of the first portion of the barcode region and the complement of the second portion of the barcode region.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for detecting a target nucleic acid, the method comprising:
   a) contacting a biological sample comprising the target nucleic acid with a templated ligation probe comprising a first part and a second part,
      wherein at least one of the first part and the second part comprises a target specific binding site which is complementary to a region of interest in the target nucleic acid,
      wherein the first part and the second part hybridize to the target nucleic acid;
   b) ligating the first and second parts using the target nucleic acid as a template, thereby generating a ligated probe;
   c) contacting the biological sample with a selector probe comprising a first strand and a second strand that form a partially double stranded probe,
      wherein the first strand comprises a first homology arm complementary to a first end of the ligated probe, a second homology arm complementary to a second end of the ligated probe, and a region that hybridizes to the second strand, and wherein the second strand comprises an insertion sequence;

d) circularizing the ligated probe using the selector probe as a template, thereby generating a circularized ligated probe comprising the insertion sequence from the second strand of the selector probe;

e) performing rolling circle amplification of the circularized ligated probe in the biological sample to generate a rolling circle amplification product; and f) detecting the rolling circle amplification product in the biological sample, thereby detecting the target nucleic acid.

2. The method of claim 1, wherein the rolling circle amplification of the circularized ligated probe is performed using a sequence of the selector probe as a primer for the rolling circle amplification.

3. The method of claim 1, wherein the first strand of the selector probe is longer than the second strand of the selector probe, and the first strand hybridizes to the second strand.

4. The method of claim 1, wherein the selector probe comprises a double stranded region and the first and second homology arms are single stranded sequences on either side of the double stranded region of the selector probe.

5. The method of claim 1, wherein the selector probe functions to circularize RNA.

6. The method of claim 1, wherein the insertion sequence comprises an insertion barcode sequence.

7. The method of claim 1, wherein the first part and/or the second part each comprises an overhang that does not hybridize to the target nucleic acid.

8. The method of claim 7, wherein the overhang comprises an adapter region.

9. The method of claim 8, wherein the adapter region does not correspond to a sequence of the target nucleic acid.

10. The method of claim 8, wherein the adapter region corresponds to a sequence of the target nucleic acid.

11. The method of claim 7, wherein the first part comprises an overhang comprising a first portion of a barcode region and the second part comprises an overhang comprising a second portion of the barcode region, wherein the barcode region comprises one or more barcode sequences.

12. The method of claim 7, wherein the overhang further comprises one or more overhang barcode sequences, and the one or more barcode sequences correspond to a sequence of the target nucleic acid.

13. The method of claim 1, wherein the selector probe is immobilized in the biological sample and/or a matrix embedding the biological sample prior to the rolling circle amplification in e), and the first strand of the selector probe is immobilized at its 5' end and is used as a primer to generate the rolling circle amplification product of the circularized ligated probe.

14. The method of claim 1, further comprising releasing the ligated probe from the target nucleic acid.

15. The method of claim 1, wherein the target nucleic acid is a target RNA, and wherein the method comprises releasing the ligated probe from the target RNA.

16. The method of claim 1, wherein the detecting comprises detecting a sequence in the sequence complementary to the circularized ligated probe, wherein the detecting comprises sequencing all or a portion of the sequence complementary to the circularized ligated probe and/or in situ hybridization to the sequence complementary to the circularized ligated probe.

17. The method of claim 1, wherein the detecting comprises:

contacting the biological sample with one or more detectably-labeled probes that directly or indirectly bind to the one or more barcode sequences or complements thereof, detecting signals associated with the one or more detectably-labeled probes, and removing the one or more detectably-labeled probe.

18. The method of claim 1, wherein the detecting comprises:

contacting the biological sample with one or more intermediate probes that directly or indirectly bind to the one or more barcode sequences or complements thereof, wherein the one or more intermediate probes are detectable using one or more detectably-labeled probes, and detecting signals associated with the one or more detectably-labeled probes.

* * * * *